United States Patent
Wang et al.

(10) Patent No.: US 10,907,209 B2
(45) Date of Patent: Feb. 2, 2021

(54) COMPOSITIONS AND METHODS FOR TREATING HEMATOLOGICAL CANCERS TARGETING THE SIRPα CD47 INTERACTION

(75) Inventors: Jean C. Y. Wang, Toronto (CA); John Dick, Toronto (CA); Jayne Danska, Toronto (CA); Liqing Jin, Toronto (CA); Alexandre Theocharides, Toronto (CA); Sujeetha Rajakumar, Toronto (CA)

(73) Assignees: UNIVERSITY HEALTH NETWORK, Toronto (CA); THE HOSPITAL FOR SICK CHILDREN, Toronto (CA)

(*) Notice: Subject to any disclaimer, the term of this patent is extended or adjusted under 35 U.S.C. 154(b) by 807 days.

(21) Appl. No.: 13/320,629

(22) PCT Filed: May 14, 2010

(86) PCT No.: PCT/CA2010/000743
§ 371 (c)(1),
(2), (4) Date: Apr. 2, 2012

(87) PCT Pub. No.: WO2010/130053
PCT Pub. Date: Nov. 18, 2010

(65) Prior Publication Data
US 2012/0189625 A1    Jul. 26, 2012

Related U.S. Application Data

(60) Provisional application No. 61/178,553, filed on May 15, 2009.

(51) Int. Cl.
*C12Q 1/6886* (2018.01)
*A61K 38/16* (2006.01)

(52) U.S. Cl.
CPC ............ *C12Q 1/6886* (2013.01); *A61K 38/16* (2013.01); *C12Q 2600/156* (2013.01)

(58) Field of Classification Search
CPC .......... A61K 6/00; A61K 38/00; A61K 38/16; A61K 38/17; A61K 38/1709; C12Q 1/00
See application file for complete search history.

(56) References Cited

U.S. PATENT DOCUMENTS

| | | | |
|---|---|---|---|
| 5,116,964 A | 5/1992 | Capon et al. | 536/27 |
| 5,580,756 A | 12/1996 | Linsley et al. | 435/69 |
| 5,844,095 A | 12/1998 | Linsley et al. | 530/387 |
| 5,869,046 A | 2/1999 | Presta et al. | 424/133 |
| 6,121,022 A | 9/2000 | Presta et al. | 435/69 |
| 6,541,615 B1 | 4/2003 | Ullrich et al. | |
| 6,913,894 B2 | 7/2005 | Bühring et al. | |
| 7,282,556 B2 | 10/2007 | Parkos | |
| 7,514,229 B2 | 4/2009 | Jamieson et al. | |
| 8,361,736 B2 | 1/2013 | Majeti et al. | |
| 9,045,541 B2 | 6/2015 | Eckelman et al. | |
| 2003/0026803 A1 | 2/2003 | Barclay | |
| 2006/0135749 A1 | 6/2006 | Matozaki et al. | |
| 2008/0051556 A1 | 2/2008 | Ullrich et al. | |
| 2008/0107654 A1 | 5/2008 | Kikuchi et al. | |
| 2010/0239578 A1* | 9/2010 | Danska | A61K 47/48415 424/134.1 |
| 2010/0239579 A1* | 9/2010 | Smith et al. | 424/134.1 |
| 2011/0014119 A1 | 1/2011 | Jaiswal et al. | |

FOREIGN PATENT DOCUMENTS

| | | |
|---|---|---|
| JP | 2006-512894 A | 4/2006 |
| JP | 2008-222711 A | 9/2008 |
| WO | WO 94/029351 | 12/1994 |
| WO | WO 99/040940 | 8/1999 |
| WO | WO 2004/096133 | 11/2004 |
| WO | 2007/092932 A2 | 8/2007 |
| WO | 2007/092932 A8 | 8/2007 |
| WO | WO 2009/046541 | 4/2009 |
| WO | WO 09/065541 | 5/2009 |
| WO | WO 2009/091547 | 7/2009 |
| WO | WO 2009/091601 | 7/2009 |
| WO | WO 2009/131453 | 10/2009 |
| WO | WO 2010/070047 | 6/2010 |
| WO | WO 2011/143624 | 11/2011 |
| WO | WO-2014/094122 A1 | 6/2014 |

OTHER PUBLICATIONS

Liu et al. (J. Mod. Biol. 365(3): 680-693, Jan. 19, 2007).*
Office Communication issued in Chinese Patent Application No. 201080021398.7, dated Jun. 6, 2013.
Extended European Search Report from related European Application No. 10774475.7, dated Sep. 9, 2012, 7 pages.
Florian, et al., "Evaluation of normal and neoplastic human mast cells for expression of CD172a (SIRPα), CD47, and SHP-1", Journal of Leukocyte Biology, vol. 77, No. 6, 2005, pp. 984-992.
Ide, et al., Role for CD47-SIRPα signaling in xenograft rejection by marcrophages, Proceedings of the National Academy of Sciences, National Academy of Sciences, US, vol. 104, No. 12, 2007, pp. 5062-5066.
Patent Examination Report from related Australian Patent Application No. 2010246872, dated Dec. 20, 2013, 5 pages.
Armour et al., "Recombinant human IgG molecules lacking FCγ receptor I binding and monocyte triggering activities", *Eur. J. Immunol.*, 29:2613-2624, 1999.
Armour et al., "The contrasting IgG-binding interactions of human and herpes simplex virus Fc receptors", *Biochemical Society Transactions*, 30(4):495-500, 2002.
International Search Report issued in PCT Application No. PCT/CA2010/000743, dated Aug. 9, 2010.

(Continued)

*Primary Examiner* — Alana Harris Dent
(74) *Attorney, Agent, or Firm* — Marshall, Gerstein & Borun LLP

(57) ABSTRACT

The invention relates to modulating the SIRPα-CD47 interaction in order to treat hematological cancer and compounds therefor. In some embodiments, there is provided methods and uses of SIRPα polypeptides, fragments and fusion proteins for treating hematological cancer, preferably human acute myeloid leukemia.

42 Claims, 11 Drawing Sheets
Specification includes a Sequence Listing.

(56) References Cited

OTHER PUBLICATIONS

Jaiswal, S. et al., "CD47 is upregulated on circulating hematopoietic stem cells and leukemia cells to avoid phagocytosis", Cell 138(2):271-85, 2009.
Majeti, R. et al., "CD47 is an adverse prognostic factor and therapeutic antibody target on human acute myeloid leukemia stem cells", Cell 138(2):286-99, 2009.
Matozaki, T. et al., "Functions and molecular mechanisms of the CD47-SIRPalpha signaling pathway", Trends Cell Biol. 19:72-80, 2009.
Ritchie, D. S. et al., "A new therapeutic target for leukemia comes to the surface", Cell 138(2):226-28, 2009.
Sano, S. et al., "Gene structure of mouse BIT/SHPS-1", Biochem. J. 344 (3):667-75, 1999.
Shultz, L. D. et al., "Multiple defects in innate and adaptive immunologic function in NOD/LtSz-scid mice", J. Immunol. 154:180-91, 1995.
Takenaka, K. et al., "Polymorphism in Sirpa modulates engraftment of human hematopoietic stem cells", Nat. Immunol. 8:1313-23, 2007.
Wang, J. C. et al., "Cancer stem cells: lessons from leukemia", Trends Cell Biol. 15:494-501, 2005.
Wines et al., "The IgC Fc Contains Distinct Fc Receptor (FcR) Binding Sites: The Leukocyte Receptors FcγRI and FcγRIIa Bind to a Region in the Fc Distinct from That Recognized by Neonatal FcR and Protein A", The Journal of Immunology, 164:5313-5318, 2000.
"Erythrocyte binging of SIRPα-Fc fusions and anti-CD47 antibodies," Experimental Report, Publication date unknown, cited in opposition period for EP 2429574 on Sep. 20, 2016.
Economides et al., "Cytokine traps: multi-component, high-affinity blockers of cytokine action," Nature Medicine, 2003, 9(1): 47-52.
EP Opposition—Information about the result of oral proceedings, Nov. 6, 2017.
Holash et al., "VEGF-Trap: A VEGF blocker with potent antitumor effects," PNAS, 2002, 99(17): 11393-11398.
International Search Report issued in International Patent Application No. PCT/NL2009/050220, dated Jun. 22, 2009.
Letter regarding the opposition procedure in European Patent application No. 10774475.7, opposed by John Gerard Leeming, issued Sep. 6, 2017.
Letter regarding the opposition procedure, submission re EU 2429574, opposed by James Poole Limited, Feb. 6, 2016.
Majeti et al., "CD47 is an adverse prognostic factor and therapeutic antibody target on human acute myeloid leukemia stem cells," Cell, 2009, 138(2): 286-299.
Nierkens et al., "Differential Requirement for CD28/CTLA-4-CD80/CD86 Interactions in Drug-Induced Type 1 and Type 2 Immune Responses to Trinitrophenyl-Ovalbumin." J Immunol, 2005, 175:3707-3714.
Opposition against European Patent No. 2429574 by James Poole Limited, filed Feb. 8, 2016.
Perrin et al., "Opposing effects of CTLA4-Ig and Anti-CD80 (B7-1) plus Anti-CD86 (B7-2) on experimental allergic encephalomyelitis," Journal of Neuroimmunology, 1996, 65:31-39.
Preliminary Observations—Summons dated Oct. 4, 2017 in Opposition Proceedings for Application No. 10774475.7.
Reply of the Patent Proprietor to the notice of opposition re EP 2429574, filed Sep. 5, 2017.
Sandborn et al., "Etanercept for Active Crohn's Disease: A Randomized Double-Blind, Placebo-Controlled Trial," Grastroenterology, 2001, 121:1088-1094.
Search Opinion issued in European Application No. 10774475.7, dated Sep. 4, 2012.
Soto-Pantoja et al., "Inhibitory signaling through signal regulatory protein-α is not sufficient to explain the antitumor activities of CD47 antibodies," PNAS, 2012, 109(42): E2842.
Supplementary Search Report issued in European Application No. 10774475.7. completed Aug. 27, 2012.

Theocharides et al., "Disruption of SIRPα signaling in macrophages eliminates human acute myeloid leukemia stem cells in xenografts," The Journal of Experimental Medicine, 2012. 209(10): 1883-1899.
Umemori et al., "Signal Regulatory Proteins (SIRPS) Are Secreted Presynaptic Organizing Molecules," The Journal of Biological Chemistry, 2008, 283(49): 34053-34061.
Untitled Document describing methodology, showing charged. Publication Date Unknown, filed in opposition period for EP 2429574 on Aug. 2, 2016.
Vernon-Wilson, et al., "CD47 is a ligand for rat macrophage membrane signal regulatory protein SIRP (OX41) and human SIRPα1," Eur. J. Immunol, 2000, 30:2130-2137.
Willingham et al., "Reply to Soto-Pantoja et al. and Zhao et al.: Targeting CD47 on human solid tumors," PNAS, 2012, 109(42): E2844-E2845.
Willingham et al., "The CD47-signal regulatory protein alpha (SIRPa) interaction is a therapeutic target for human solid tumors," PNAS, 2012, 109(17): 6662-6667.
Zhao et al., "Is targeting of CD47-SIRPα enough for treating hematopoietic malignancy?" Blood, 2012, 119(18): 4333-4334.
Zhao et al., European Journal of Clinical Investigation, 2009, 39 (Suppl. 1), Abstract 636.
Barazi et al., Regulation of integrin function by CD47 ligands. Differential effects on alpha vbeta 3 and alpha 4beta1 integrin-mediated adhesion, J. Biol. Chem., 277:42859-66 (2002).
Brooke et al., Human Lymphocytes Interact Directly with CD47 through a Novel Member of the Signal Regulatory Protein (SIRP) Family, J. of Immunology, 173:2562-2570 (2004).
Chung et al., Thrombspondin acts via integrin-associated protein to activate the platelet integrin alphaIIbbeta3, J. Biol. Chem., 272:14740-6 (1997).
Decision Revoking European Patent No. EP-B-2429574 and Grounds for the decision, dated Jan. 2, 2018.
DePalma et al., Tie2 identifies a hematopoietic lineage of proangiogenic monocytes requested for tumor vessel formation and a mesenchymal population of pericyte progenitors, Can. Cell, 8:211 (2005).
Gao et al., Thrombospondin modulates alpha v beta 3 function through integrin-associated protein, J. Cell Biol., 135:533-44 (1996a).
Gardai et al., Cell-Surface Calreticulin Initiates Clearance of Viable or Apoptotic Cells through trans-Activation of LRP on the Phagocyte, Cell, 123:321-34 (2005).
Isenberg et al., CD47 is necessary for inhibition of nitric oxidestimulated vascular cell responses by thrombospondin-1, J. Biol. Chem., 281:26069-80 (2006).
Latour et al., Bidirectional Negative Regulation of Human T and Dendritic Cells by CD47 and Its Cognate Receptor Signal-Regulator Protein-α: Down-Regulation of IL-12 Responsiveness and Inhibition of Dendritic Cell Activation, J. Immunol., 167:2547-54 (2001).
Lee et al ., Novel Structual Determinants on SIRP α that Mediate Binding to CD47, J. Immunol., 179-7741-50 (2007).
Lewis et al., Distinct role of macrophages in different tumor microenvironments, Cancer Res., 66(2): 605-12 (2006).
Lin et al., Colony-stimulating factor 1 Promotes Prgression of Mammary Tumors to Malignancy, J. Exp. Med., 193(6):727-39 (2001).
Lindberg et al., Decreased resistance to bacterial infection and granulocyte defects in IAP-deficient mice, Science, 274:795-8 (1996).
Liu et al., Peptide-Mediated Inhibition of Neutrophil Transmigration by Blocking CD47 Interactions with Signal Regulatory Protein $\alpha^1$, J. Immunol., 172: 2578-2585 (2004).
Liu et al., Pre-Clinical Development of a Humanized Anti-CD47 Antibody with Anti-Cancer Therapeutic Potiential, pLOS One, 10(9): e0137345 (2015).
Liu et al., Signal Regulatory Protein (SIRPα), a Cellular Ligand for CD47, Regulates Neutrophil Transmigration, J. Biol. Chem., 277(12): 10028-36 (2002).
Manna et al., The Mechanism of CD47-Dependent Killing of T Cells: Heterotrimeric Gi-Dependent Inhibition of Protein Kinase A, J. Immunol., 170:3544-53 (2003).
Mantovani et al., Role of tumor-associated macrophages in tumor progression and invasion, Cancer Metastasis Rev., 25(3):315-22 (2006).

(56) References Cited

OTHER PUBLICATIONS

Murdoch et al., Expression of Tie-2 by Human Monocytes and Their Responses to Angiopoietin-2, *J. Immunol.*, 178:7405-411 (2007).
Oldenborg et al., CD47-Signal Regulatory Protein α (SIRPα) Regulates Fcγ and Complement Receptor-mediated Phagocytosis, *J. Exp. Med.*, 193(7):855-61 (2001).
Oldenborg et al.,. Role of CD47 as a Marker of Self on Red Blood Cells, *Science*, 288(5473): 2051-54 (2000).
Olsson et al., Dose-dependent inhibitory effect of CD47 in macrophage uptake of IgG-opsonized murine erythrocytes, *Biochem. Biophys. Res. Commun.*, 352:193-7 (2007).
Petrova et al., TTI-621 (SIRPαFc): A CD47-Blocking Innate Immune Checkpoint Inhibitor with Broad Antitumor Activity and Minimal Erythrocyte Binding, *Clin. Cancer Res.*, 23:1068 (2017).
Piccione et al., SIRPα-Antibody Fusion Proteins Selectively Bind and Eliminate Dual Antigen-Expressing Tumor Cells, *Clinical Cancer Res.*, 22: 5109-19 (2016).
Pietsch et al., Anti-leukemic activity and tolerability of anti-human CD47 monoclonal antibodies, *Blood Can. J.*, 7:e536 (2017).
Sarfati et al., CD47 in the immune response: role of thrombospondin and SIRP-alpha reverse signaling, *Curr. Drug Targets*, 9:842-50 (2008).
Subramanian et al., Species-and cell type-specific interactions between CD47 and human SIRPα, *Blood*, 107(6):2548-56 (2006).
Wang et al., Attenuation of phagocytosis of xenogeneic cells by manipulating CD47, *Blood*, 109:836-42 (2007).
Wang et al., Integrin-associated protein stimulates alpha2beta1-dependent chemotaxis via Gi-mediated inhibition of adenylate cyclase and extracellular-regulated kinases, *J. Cell Biol.*, 147:389-400 (1999).
Yuan et al., Pathophysiology of Tumor-Associated Macrophages, *Adv. Clin. Chem.*, 45: 199 (2008).
Lamy, et al., "CD47 and the 19 kDa Interacting Protein-3 (BNIP3) in T Cell Apoptosis*", The Journal of Biological Chemistry, vol. 278, No. 26, Issue of Jun. 27, 2003, pp. 23915-23921.
Petrova, et al., "Lack of CD47 membrane mobility contributes to the poor erythrocyte binding of SIRPαFc, a novel CD47-blocking cancer immunotherapeutic", American Association for Cancer Research, Annual Meeting, Philadelphia, 2015, presentation abstract, 2 pages.
Pettersen, et al., "CD47 Signals T Cell Death", J. Immunol, No. 162, 1999, pp. 7031-7040.
Uger, et al., "Cancer immunotherapy targeting CD47: Wild type SIRPαFc is the ideal CD47-blocking agent to minimize unwanted erythrocyte binding", American Association for Cancer Research, Annual Meeting, San Diego, 2014, presentation abstract, 1 page.
Van, et al., "CD47$^{low}$ Status on CD4 Effectors Is Necessary for the Contraction/Resolution of the Immune Response in Humans and Mice", PLoS One, vol. 7, Issue 8, e41972, Aug. 2012, pp. 1-10.
Majeti, "CD47 Is an Independent Prognostic Factor and Therapeutic Antibody Target on Human Acute Myeloid Leukemia Stem Cells", Blood, (ASH Annual Meeting Abstracts), No. 112: Abstract 766, 2008, 3 pages.
Office Action from related Japanese Application No. 2012-510083, dated Jun. 24, 2014, 12 pages.
Opposition filed by John Gerard Leeming in related European Application No. 10774475.7 dated Feb. 8, 2016, 95 pages.
Experimental Report, cited as D10 in Opposition filed by John Gerard Leeming in related European Application No. 10774475.7 dated Feb. 8, 2016, 6 pages.
Communication filed in related European Application No. 10774475.7 dated Mar. 29, 2013, 4 pages.
Communication filed in related European Application No. 10774475.7 dated Jun. 12, 2014, 4 pages.
Barclay et al., "The SIRP family of receptors and immune regulation", Nature Reviews, dated Jun. 2006, vol. 6, pp. 457-463.
Opposition filed by James Poole Limited in related European Application No. 10774475.7 dated Feb. 8, 2016, 99 pages.
Ronald Reid, "Peptide and Protein Drug Analysis", p. 616, 2000.
Seiffert et al., "Signal-regulatory protein α (SIRPα) but not SIRPβ is involved in T-cell activation, binds to CD47 with high affinity, and is expressed on immature CD34+CD38− hematopoietic cells", Blood, May 1, 2001, vol. 97, No. 9, pp. 2741-2749.
Jaiswal et al., "Macrophages as mediators of tumor immunosurveillance", Trends Immunol., Jun. 2010; vol. 31, No. 6, pp. 212-219.
European Search Report and Search Opinion in related European Application No. 15160169.7, dated Dec. 1, 2015, 7 pages.
Translation of Office Action issued in related Japanese Application No. JP 2015-160462, dated Jun. 8, 2016, 5 pages.

\* cited by examiner

B

A

Figure 5
A
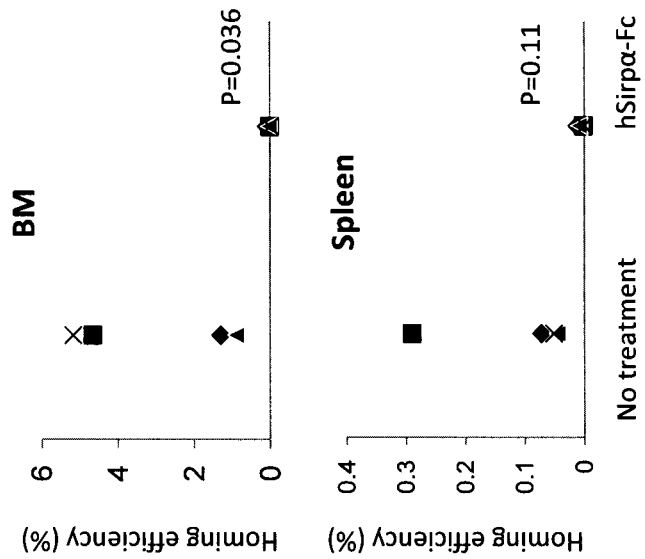
B
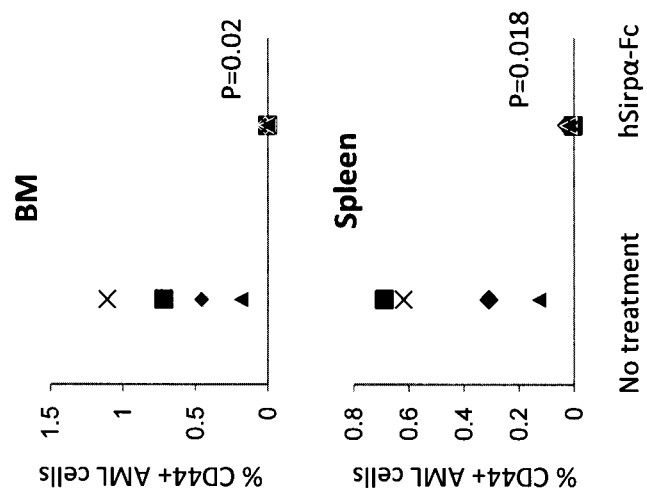

Figure 8

```
  1 MEPAGPAPGRLGPLLLLLCLLLPGLLLSASSCFCTGATRTEVKLKVTHIQPEKSVSV  NOD
  1 MEPAGPAPGRLGPLLLLLCLLLPGLLLSASSCFCTGATGKELLIHVTFSYHFPEKSV  NOR
  1 MEPAGPAPGRLGPLLLLLCLLLPGLLLSASSCFCTGATGKELLIHVTFSYHFPEKSV  B6

46 AAGDSTVLNCTLTSLLLPVGPIRWYRGVGPSRLLIHYSFTKVTQPEYVPRVI       NOD
 46 AAGDSTVLNCTLTSLLLPVGPIRWYRGVGPSRLLIHYSFTKVTQPEYVPRVI       NOR
 46 AAGDSTVLNCTLTSLLLPVGPIRWYRGVGPSRLLIHYSFTKVTQPEYVPRVI       B6

91 TNVSDATKRSNLDFSIRIHSNVTPEDAGTYYCVKFQRLLISFAGSS-IEPDTEI    NOD
 91 RNVSDTTKRSNMDFSIRIHSNVTPADAGIYYCVKFQKGSSE-SSEPDTEI        NOR
 91 RNVSDTTKRSNMDFSIRIHSNVTPADAGIYYCVKFQKGSSE-SSEPDTEI        B6

134 QSGGGGTEVYVLAKPSPPEELETTVKNZNFTCKSHGFSPRNN                NOD
136 QSGGGGTEVYVLAKPSPPEELETTVKNZNFTCKSHGFSPRNN                NOR
136 QSGGGGTEVYVLAKPSPPEELETTVKNZNFTCKSHGFSPRNN                B6

(Figure 8 – Sequence alignment of NOD, NOR, and B6 across positions 1–316)
```

```
359 Q T F P G N N A T H N W N V F I G V G V A C A L L V V L L M A A A L Y L L R I H I K Q K K A K G   NOD
361 Q T F P D N N A T H N W N V F I G V G V A C A L L V V L L M A A A L Y L L R I H I K Q K K A K G   NOR
361 Q T F P D N N A T H N W N V F I G V G V A C A L L V V L L M A A A L Y L L R I H I K Q K K A K G   B6

404 S T S S T R L H E P E K N A R E I T Q I H Q - - - D T N D I N D D I T Y A D L N L P K K E K K     NOD
406 S T S S T R L H E P E K N A R E I T Q I H Q - - - D T N D I N D D I T Y A D L N L P K K E K K     NOR
406 S T S S T R L H E P E K N A R E I T Q V Q S L I Q D T N D I N D D I T Y A D L N L P K K E K K     B6

445 P A P R A P E P N N H T E Y A S I E T G K V P R P E D T L T T Y A D L D M V H L S R A Q P A Q P A   NOD
447 P A P R A P E P N N H T E Y A S I E T G K V P R P E D T L T T Y A D L D M V H L S R A Q P A Q P A   NOR
451 P A P R A P E P N N H T E Y A S I E T G K V P R P E D T L T T Y A D L D M V H L S R A Q P A Q P A   B6

490 P K P E P S F S E Y A S V Q V Q R K   NOD (SEQ ID 1)
492 P K P E P S F S E Y A S V Q V Q R K   NOR (SEQ ID 2)
496 P K P E P S F S E Y A S V Q V Q R K   B6  (SEQ ID 3)
```

COMPOSITIONS AND METHODS FOR TREATING HEMATOLOGICAL CANCERS TARGETING THE SIRPα CD47 INTERACTION

RELATED APPLICATIONS

The present application is a national phase application under 35 U.S.C. § 371 of International Application No. PCT/CA2010/000743 filed May 14, 2010 which claims priority to U.S. Provisional Application 61/178,553 filed May 15, 2009, the entire text and figures of which disclosures are incorporated herein by reference without disclaimer.

FIELD OF THE INVENTION

The invention relates to targeting the SIRPα-CD47 interaction in order to treat hematological cancer, particularly human acute myeloid leukemia (AML), and compounds therefor.

BACKGROUND OF THE INVENTION

Graft failure in the transplantation of hematopoietic stem cells occurs despite donor-host genetic identity of human leukocyte antigens, suggesting that additional factors modulate engraftment. With the non-obese diabetic (NOD)-severe combined immunodeficiency (SCID) xenotransplantation model, it was recently found that the NOD background allows better hematopoietic engraftment than other strains with equivalent immunodeficiency-related mutations (Takenaka, K. et al. Polymorphism in Sirpa modulates engraftment of human hematopoietic stem cells. *Nat. Immunol.* 8, 1313-1323 (2007)). Polymorphisms in the Sirpa allele were identified and shown to be responsible for the differences in engraftment between the mouse strains analyzed. While the NOD background conferred the best support for human engraftment, mice with other polymorphisms of Sirpa could not be engrafted (i.e. NOD.NOR-Idd13.SCID). In mouse and human, Sirpa encodes for the SIRPα protein which interacts with its ligand CD47. In the hematopoietic system, SIRPα is mainly found on macrophages, dendritic cells, and granulocytes, while CD47 is present on most hematopoietic cells (Matozaki, T., Murata, Y., Okazawa, H. & Ohnishi, H. Functions and molecular mechanisms of the CD47-SIRPalpha signalling pathway. *Trends Cell Biol.* 19, 72-80 (2009)). It was shown that the murine Sirpa allele is highly polymorphic in the extracellular immunoglobulin V-like domain which interacts with CD47. Thirty-seven (37) unrelated normal human controls were sequenced and 4 polymorphisms were identified, suggesting that the Sirpa allele is polymorphic in humans as it is in mice (Takenaka et al. supra).

A large body of work has shown that human acute myeloid leukemia (AML) clones are hierarchically organized and maintained by leukemia initiating cells (AML-LSC) (Wang, J. C. & Dick, J. E. Cancer stem cells: lessons from leukemia. *Trends Cell Biol.* 15, 494-501 (2005)). However, little is known about molecular regulators that govern AML-LSC fate. CD47 is expressed in most human AML samples, but the level of expression on leukemic blasts varies. CD47 expression is higher on human AML LSCs compared to normal HSCs (Majeti, R. et al, CD47 is an adverse prognostic factor and therapeutic antibody target on human acute myeloid leukemia stem cells. *Cell* 138, 286 (2009)). Higher CD47 expression has been shown to be an independent poor prognostic factor in AML (Majeti et al., supra). Treatment of immune-deficient mice engrafted with human AML with a monoclonal antibody directed against CD47 results in reduction of leukemic engraftment in the murine bone marrow (Majeti et al., supra). However, it is not clear if this effect is specifically mediated through disruption of CD47-SIRPα interactions, as CD47 also binds to SIRPγ and to the integrin β3 subunit (Matozaki et al., supra).

SUMMARY OF THE INVENTION

According to one aspect, there is provided a method for treating hematological cancer comprising modulating the interaction between human Sirpα and human CD47. Preferably, the interaction between human Sirpα and human CD47 is modulated by administering a therapeutically effective amount of a polypeptide capable of binding to the extracellular domain of human CD47.

According to a further aspect, there is provided a use of a compound for treating hematological cancer, the compound comprising a polypeptide capable of modulating the interaction between human Sirpα and human CD47 by binding to the extracellular domain of human CD47.

According to a further aspect, there is provided a use of a compound in the preparation of a medicament for treating hematological cancer, the compound comprising a polypeptide capable of modulating the interaction between human Sirpα and human CD47 by binding to the extracellular domain of human CD47.

In preferable aspects, the polypeptide comprises soluble human Sirpα, or a CD47 binding fragment thereof. In some embodiments, the polypeptide is the extracellular domain of human Sirpα.

In one embodiment the polypeptide is a Sirpα-Fc fusion protein, and is preferably SEQ ID NO. 13.

According to a further aspect, there is provided a method of determining genetic polymorphisms in humans affecting survival to hematological cancer, comprising:
  a) sequencing the Sirpα gene from a plurality of humans having hematological cancer;
  b) determining nucleotide differences in the Sirpα gene within the plurality of humans; and
  c) correlating the nucleotide differences with survival to determine relevant polymorphisms.

In a further aspect, there is provided a method of prognosing likelihood of survival to hematological cancer comprising:
  a) sequencing the Sirpα gene from the recipient; and
  b) determining whether the relevant polymorphisms described herein exist.

According to some embodiments, the polypeptide capable of modulating the interaction between human Sirpα and human CD47 is selected from the group consisting of:
  a) a polypeptide consisting of the amino acid sequence of SEQ ID NO. 1;
  b) a polypeptide consisting of a CD47-binding fragment of the amino acid sequence of SEQ ID NO, 1, wherein the fragment comprises at least one of residues 31, 32, 34, 37, 74, 77, 83, 84, 86, 87, 90, 91, 96, 100, 102, 114, 118, 126 of SEQ m NO. 1; and
  c) a CD47-binding variant of one of the polypeptide in a) and b) with up to 1 amino acid insertion, deletion or substitution for every 7 amino acids in length of the polypeptide, wherein the polypeptide comprises at least one of residues 31, 32, 34, 37, 74, 77, 83, 84, 86, 87, 90, 91, 96, 100, 102, 114, 118, 126 of SEQ ID NO. 1.

According to another embodiment, the polypeptide capable of modulating the interaction between human Sirpα and human CD47 is selected from the group consisting of:
  a) a polypeptide consisting of the amino acid sequence of SEQ ID NO, 2;
  b) a polypeptide consisting of a CD47-binding fragment of the amino acid sequence of SEQ ID NO. 2; and
  c) a CD47-binding variant of one of the polypeptide in a) and b) with up to 1 amino acid insertion, deletion or substitution for every 7 amino acids in length of the polypeptide;
  wherein:
  i. at least one of residues at positions 31, 32, 34, 37, 74, 77, 83, 84, 86, 87, 90, 91, 96, 100, 102, 114, 118, 126 of SEQ ID NO. 2 in the polypeptide is replaced with corresponding residues 31, 32, 34, 37, 74, 77, 83, 84, 86, 87, 90, 91, 96, 100, 102, 114, 118, 126 of SEQ ID NO. 1; or
  ii. at least one of residues 129 and 130 of SEQ ID NO. 2 in the polypeptide is deleted.

According to another embodiment, the polypeptide capable modulating the interaction between human Sirpα and human CD47 is selected from the group consisting of:
  a) a polypeptide consisting of an amino acid sequence selected from the group consisting of SEQ ID NOS. 4-7;
  b) a polypeptide consisting of a CD47-binding fragment of an amino acid sequence selected from the group consisting of SEQ ID NOS. 4-7; and
  c) a CD47-binding variant of one of the polypeptide in a) and b) with up to 1 amino acid insertion, deletion or substitution for every 7 amino acids in length of the polypeptide.

According to a further aspect, there is provided a pharmaceutical composition for treating a hematological cancer, preferably leukemia, and further preferably human acute myeloid leukemia (AML), comprising an effective amount of a polypeptide described herein and a pharmaceutically acceptable carrier.

In preferable aspects, the hematological cancer preferably comprises a CD47+ presenting cancer cell or tumour.

BRIEF DESCRIPTION OF FIGURES

These and other features of the preferred embodiments of the invention will become more apparent in the following detailed description in which reference is made to the appended drawings wherein:

FIG. 5 shows that in vitro pre-incubation of human SIRPα (V2) fusion protein blocks homing of primary AML cells into NOD.SCID mouse bone marrow (BM) and spleen. A) The percentage of human CD44+ AML cells in BM and spleen was measured by flow cytometry using murine anti-human antibodies. Each symbol represents a different mouse. B) Homing efficiency of AML cells to NOD.SCID BM and spleen was calculated as [Total #AML cells recovered]/[Total #AML cells injected]×100.

FIG. 8 illustrates the protein sequence alignment of murine SIRPα disclosed in WO 09/046541. cDNA prepared from BM-derived macrophages was used as a template for PCR amplification of Sirpα transcripts from NOD and NOR mice. The B6 mouse sequence is from the EnsEMBL database.

FIG. 9 illustrates protein sequence alignments of murine and human SIRPα IgV domains disclosed in WO 09/046541. (a) cDNA prepared from BM macrophages was used as a template for PCR amplification of Sirpα transcripts from NOD and NOR mice. The C57BL/6 (B6), BALB/c and 129/Sv sequences were obtained from EnsEMBL and NCBI databases. Open boxes represent b-pleated sheets identified in the X-ray crystal structure of SIRPα and correspond to similar regions in the Ig heavy chain variable region. Amino acids that vary between mouse strains are shaded. B6 was used as the parental sequence. (b) Exon 3 of SIRPα containing the IgV domain was PCR amplified from genomic DNA of 37 individuals from the human HapMap phase 1 release. Open boxed regions represent the same features as in (a), with V1 serving as the parental sequence.

DETAILED DESCRIPTION

Figure 1:
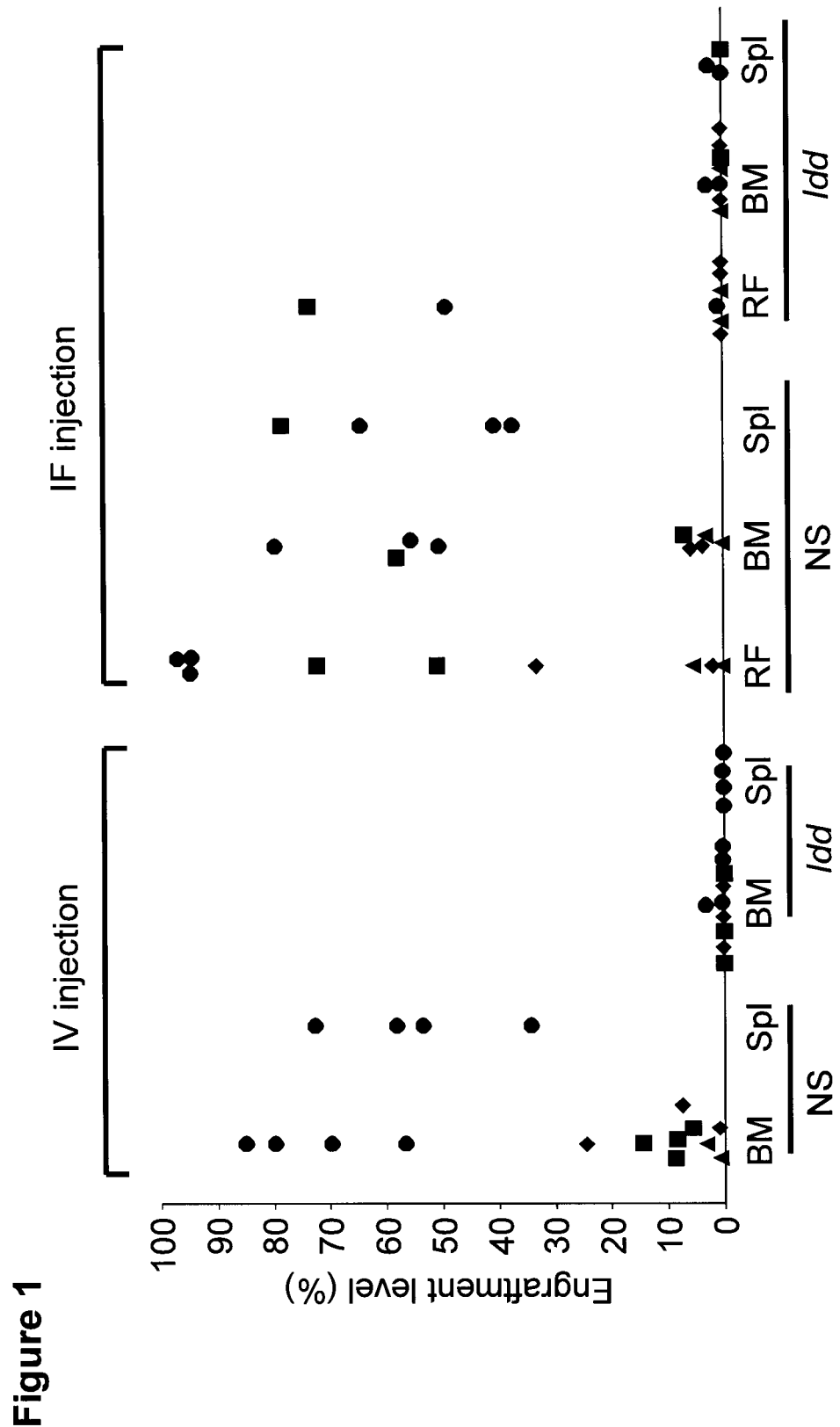
FIG. 1 shows NOD.SCID mice carrying the NOR-Idd13 locus (NOD.NOR-Idd13.SCID) do not support repopulation by human AML-LSC. Y axis displays percentage of human engraftment in the injected right femur (RF), marrow from bones at non-injected sites (BM), or spleen (Spl) of NOD.SCID (NS) and NOD.NOR-Idd13.SCID (Idd) mice 7-8 weeks after injection of primary AML cells from 4 patients. $3 \times 10^6$ cells were introduced into each mouse either by intravenous (IV) or intrafemoral (IF) injection. Mice transplanted with the same patient sample are indicated by the same shape of symbol.

In the following description, numerous specific details are set forth to provide a thorough understanding of the invention. However, it is understood that the invention may be practiced without these specific details.

Applicant shows that CD47-SIRPα interaction modulates homing and engraftment of human AML-LSC in a xenotransplant model. Interruption of CD47-SIRPα signaling through targeting of either CD47 or SIRPα is a potential therapeutic approach for eradication of hematological CD47+ cancer cells and tumours, including cancer stem cells, such as AML-LSC in patients.

As used herein "cancer stem cell" refers to cancer cells found within tumors and hematological cancers, for example AML where the cancer stem cells are termed leukemic stem cells (AML-LSC), that are biologically distinct from the bulk tumor cells and possess characteristics associated with stem cells, specifically the ability to self renew and to propagate and give rise to all cell types found in a particular cancer sample.

As used herein "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer., Principles of Protein Structure, Springer-Verlag). Examples of amino acid groups defined in this manner include:
  (i) a charged group, consisting of Glu and Asp, Lys, Arg and His,
  (ii) a positively-charged group, consisting of Lys, Arg and His,
  (iii) a negatively-charged group, consisting of Glu and Asp,
  (iv) an aromatic group, consisting of Phe, Tyr and Trp,
  (v) a nitrogen ring group, consisting of His and Trp,
  (vi) a large aliphatic nonpolar group, consisting of Val, Leu and Ile,
  (vii) a slightly-polar group, consisting of Met and Cys,
  (viii) a small-residue group, consisting of Ser, Thr, Asp, Asn, Gly, Ala, Glu, Gln and Pro,
  (ix) an aliphatic group consisting of Val, Leu, Ile, Met and Cys, and
  (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

As used herein "engrafting" a cell, for example a cancer stem cell and preferably a human acute myeloid leukemic stem cell, means placing the stem cell into an animal, e.g., by injection, wherein the cell persists in vivo. This can be readily measured by the ability of the cancer stem cell, for example, to propagate.

As used herein "fragment" relating to a polypeptide or polynucleotide means a polypeptide or polynucleotide consisting of only a part of the intact polypeptide sequence and structure, or the nucleotide sequence and structure, of the reference gene. The polypeptide fragment can include a C-terminal deletion and/or N-terminal deletion of the native polypeptide, or can be derived from an internal portion of the molecule. Similarly, a polynucleotide fragment can include a 3' and/or a 5' deletion of the native polynucleotide, or can be derived from an internal portion of the molecule.

As used herein "fusion protein" refers to a composite polypeptide, i.e., a single contiguous amino acid sequence, made up of two (or more) distinct, heterologous polypeptides which are not normally or naturally fused together in a single amino acid sequence. Thus, a fusion protein may include a single amino acid sequence that contains two entirely distinct amino acid sequences or two similar or identical polypeptide sequences, provided that these sequences are not normally found together in the same configuration in a single amino acid sequence found in nature. Fusion proteins may generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art. Fusion proteins may also contain a linker polypeptide in between the constituent polypeptides of the fusion protein. The term "fusion construct" or "fusion protein construct" is generally meant to refer to a polynucleotide encoding a fusion protein. In one embodiment, the fusion protein is a polypeptide as described herein fused to a portion of an Ig molecule. The Ig portion of the fusion protein can include an immunoglobulin constant region, e.g. a human Cγ1 domain or a Cγ4 domain (e.g. the hinge, CH2, and CH3 regions of human IgCγ1 or human IgCγ4 (see e.g., Capon et al., U.S. Pat. Nos. 5,116,964; 5,580,756; 5,844,095, and the like). In one preferred embodiment, Ig fusion proteins include a polypeptide as described herein coupled to an immunoglobulin constant region (e.g., the Fc region).

In embodiments where the polypeptide is coupled to the Fc domain, the Fc domain may be selected from any immunoglobulin (e.g. an IgG such as $IgG_1$ or IgG2a or IgG4). Desirably, the selected Fc domain is modified (e.g. by amino acid substitution(s) at residues critical for binding with Fc receptors) to reduce or prevent binding to Fc receptors in vivo (i.e. the modified Fc domain preferably shows a reduced affinity for binding endogenous Fc receptors other than neonatal Fc receptors (FcRn), including, for example, FcγRI, FcγRII and FcγRIII). As well, the selected Fc domain is desirably modified to alter effector function, such as to reduce complement binding and/or to reduce or abolish complement dependent cytotoxicity. Such modifications have been extensively described by, for example, Clark and colleagues, who have designed and described a series of mutant IgG1, IgG2 and IgG4 Fc domains and their FcγR binding properties (Armour et al., 1999; Armour et al., 2002, the content of which is incorporated herein by reference in this application). For example, one or more amino acids at positions selected from 234, 235, 236, 237, 297, 318, 320 and 322 can be substituted to alter affinity for an effector ligand, such as an Fc receptor or the C1 component of complement, as reported in further detail by Winter et al in U.S. Pat. Nos. 5,624,821 and 5,648,260. Also, one or more amino acids at positions 329, 331 and 322 can be substituted to alter C1q binding and/or reduce or abolish CDC, as described for instance in U.S. Pat. No. 6,194,551. In one especially preferred modified Fc domain, the Fc domain is derived from $IgG_1$ (Wines et al., 2000) and comprises amino acid modification at amino acid 234 and/or 235, namely $Leu^{234}$ and/or $Leu^{235}$. These leucine residues are within the lower hinge region of $IgG_1$ where the Fc receptor engages with the Fc domain. One or both of the leucine residues may be substituted or deleted to prevent Fc receptor engagement (i.e. binding); for example, one or both of $Leu^{234}$ and $Leu^{235}$ may be substituted with alanine (i.e. L234A and/or L235A) or another suitable amino acid(s) (Wines et al., 2000).

In other embodiments, the half life of the fusion protein is improved by incorporating one more amino acid modifications, usually in the form of amino acid substitutions, for instance at residue 252, e.g., to introduce Thr, at residue 254, e.g., to introduce Ser, and/or at residue 256 e.g., to introduce Phe. Still other modifications can be made to improve half-life, such as by altering the CH1 or CL region to introduce a salvage receptor motif, such as that found in the two loops of a CH2 domain of an Fc region of an IgG. Such alterations are described for instance in U.S. Pat. Nos. 5,869,046 and 6,121,022.

Altered C1q binding, or reduced complement dependent cytotoxicity, can be introduced by altering constant region amino acids at locations 329, 331 and 322, as described in U.S. Pat. No. 6,194,551. The ability of the antibody to fix complement can further be altered by introducing substitutions at positions 231 and 239 of the constant region, as described in WO94/029351.

As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplastic syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

The term "CD47+" is used with reference to the phenotype of cells targeted for binding by the present polypeptides. Cells that are CD47+ can be identified by flow cytometry using CD47 antibody as the affinity ligand. The cells examined for CD47 phenotype can include standard tumour biopsy samples including particularly blood samples taken from the subject suspected of harbouring CD47+ cancer cells.

The term "macrophage desupression" or "desupression of macrophages" as used herein refers to the desupression, removal of inhibition, increase or initiation of the role, activity and/or effect of macrophages.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "polypeptide" and "protein" are used interchangeably and mean proteins, protein fragments, modified proteins, amino acid sequences and synthetic amino acid sequences. The polypeptide can be glycosylated or not.

As used herein, "prognosing" as used herein means predicting or identifying the clinical outcome in a subject. A prognosis includes providing an indication of disease progression and also includes providing an indication of likelihood of death due to a disease or condition.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

According to one aspect, there is provided a method for treating hematological cancer comprising modulating the interaction between human Sirpα and human CD47. Preferably, the interaction between human Sirpα and human CD47 is modulated by administering a therapeutically effective amount of a polypeptide capable of binding to the extracellular domain of human CD47.

According to a further aspect, there is provided a use of a compound for treating hematological cancer, the compound comprising a polypeptide capable of modulating the interaction between human Sirpα and human CD47 by binding to the extracellular domain of human CD47.

According to a further aspect, there is provided a use of a compound in the preparation of a medicament for treating hematological cancer, the compound comprising a polypeptide capable of modulating the interaction between human Sirpα and human CD47 by binding to the extracellular domain of human CD47.

In some embodiments, the polypeptide comprises soluble human Sirpα, or a fragment thereof, preferably the polypeptide is the extracellular domain of human Sirpα.

In some embodiments, the polypeptide is fused to a second protein, preferably, the Fc portion of IgG. Preferably, the resulting fusion protein is SEQ ID NO. 13.

In some embodiments, the modulation results in desupression of macrophages.

In some embodiments, the hematological cancer is leukemia, preferably selected from acute lymphocytic leukemia, acute myeloid leukemia, chronic lymphocytic leukemia, chronic myelogenous leukemia, and myelodysplastic syndrome, preferably, human acute myeloid leukemia.

In other embodiments, the hematological cancer is a lymphoma or myeloma selected from Hodgkin's lymphoma, both indolent and aggressive non-Hodgkin's lymphoma, Burkitt's lymphoma, follicular lymphoma (small cell and large cell), multiple myeloma (MM), giant cell myeloma, heavy-chain myeloma, and light chain or Bence-Jones myeloma.

It is presently shown that interruption of SIRPα-CD47 interactions in AML results in impaired homing, engraftment, and migration of AML cells. These effects are mediated through improved innate immune surveillance by macrophages in the host bone marrow microenvironment. This therapeutic approach will likely be effective for other hematologic cancers that occupy a bone marrow microenvironmental niche.

Figure 9:
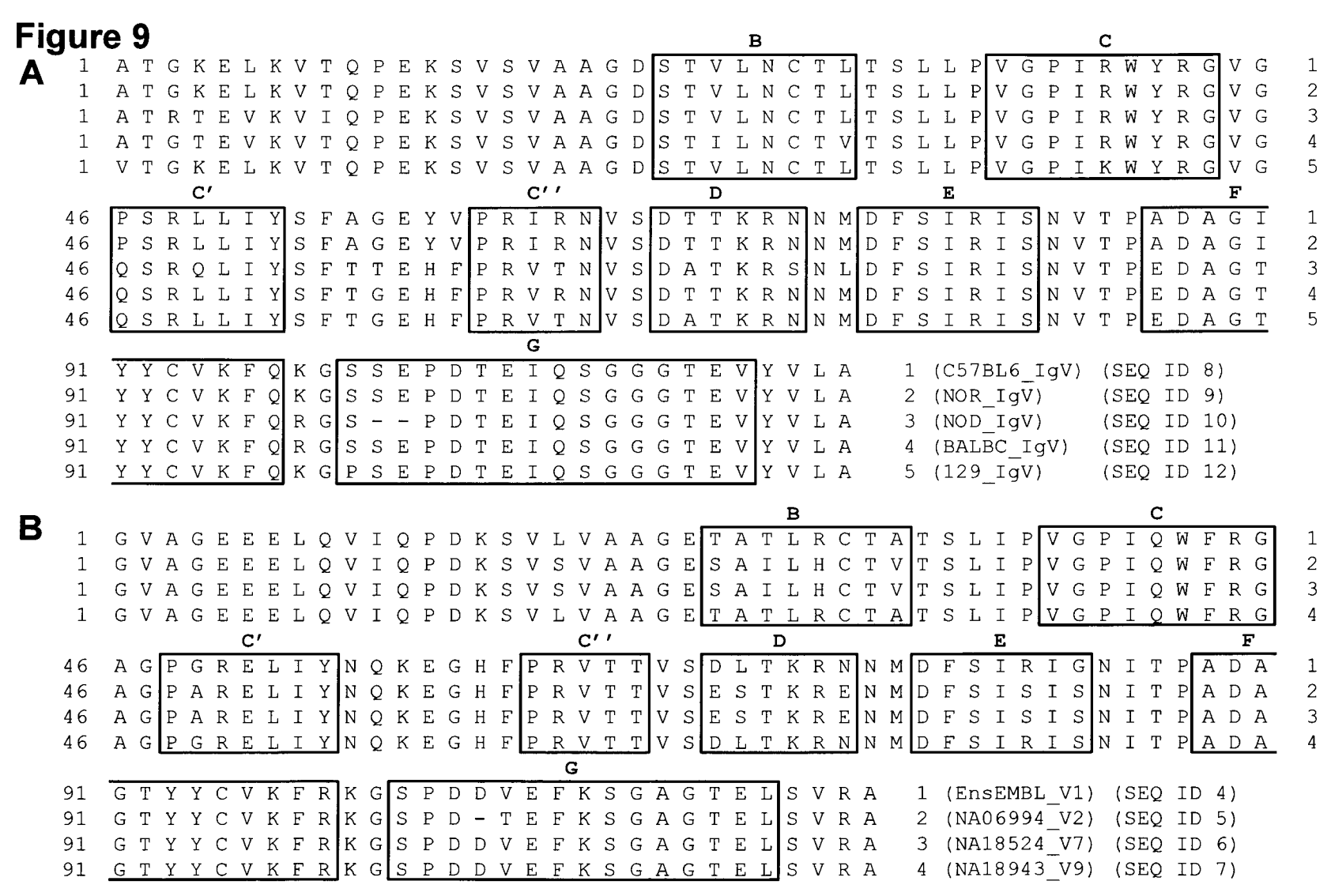

WO 09/065541 describes that polymorphisms in SIRPα confer differential capacity of NOD macrophages to support human hematopoiesis. The protein sequence alignments of SIRPα described in WO 09/065541 are presently reproduced as FIGS. 8 and 9. cDNA prepared from BM-derived macrophages was used as a template for PCR amplification of Sirpα transcripts from NOD and NOR mice. Comparison of the Sirpα coding sequence between NOD and NOR revealed 24 amino acid differences, 20 of these in the extracellular IgV-like domain of molecule where the NOD sequence displays 18 substitutions and two deletions compared to NOR and B6. This observed variation in the Sirpα the N-terminal IgV-like domain between NOD and NOR or B6 is more extensive than that previously reported in this region amongst the B6, BALB/c and 129/Sv strains (Sano, S. et al. (1999) *Biochem J* 344 Pt 3, 667-75).

WO 09/065541 further describes that polymorphisms in SIRPα confers differential binding to human CD47. WO 09/065541 describes the sequencing of SIRPα IgV domain from 37 unrelated normal Caucasian (CEU), African (YRI), Chinese (CHB) and Japanese (JPT) individuals from the human HapMap genome project and identified 4 distinct SIRPα IgV alleles reflecting combinatorial variation at 18 amino acids, reproduced herein as FIG. 9. Applicants observed human allelic variations at predicted CD47 binding residues and in the same sub-regions of the SIRPα IgV domain that distinguish NOD from NOR alleles. WO 09/065541 further teaches that human CD47 binding to NOD-derived SIRPα IgV domain is very high and predictive of engraftment of human stem cells and that this effect is mediated through CD47-SIRPα signaling.

Accordingly there is provided, a method of determining genetic polymorphisms in humans affecting survival to hematological cancer, comprising:
 a) sequencing the Sirpα gene from a plurality of humans having hematological cancer;
 b) determining nucleotide differences in the Sirpα gene within the plurality of humans; and
 c) correlating the nucleotide differences with survival to determine relevant polymorphisms.

In a further aspect, there is provided a method of prognosing likelihood of survival to hematological cancer comprising:
 a) sequencing the Sirpα gene from the recipient; and
 b) determining whether the relevant polymorphisms described herein exist.

In some embodiments, the nucleotide differences result in amino acid differences, preferably at least one of:
 a) replacement of at least one of residues at positions 31, 32, 34, 37, 74, 77, 83, 84, 86, 87, 90, 91, 96, 100, 102, 114, 118, 126 of SEQ ID NO. 2 with corresponding residues 31, 32, 34, 37, 74, 77, 83, 84, 86, 87, 90, 91, 96, 100, 102, 114, 118, 126 of SEQ ID NO. 1; or
 b) deletion of at least one of residues 129 and 130 of SEQ ID NO. 2.

Further, according to some embodiments, the polypeptide capable modulating the interaction between human Sirpα and human CD47 is selected from the group consisting of:
 a) a polypeptide consisting of the amino acid sequence of SEQ ID NO. 1;
 b) a polypeptide consisting of a CD47-binding fragment of the amino acid sequence of SEQ ID NO. 1, wherein the fragment comprises at least one of residues 31, 32, 34, 37, 74, 77, 83, 84, 86, 87, 90, 91, 96, 100, 102, 114, 118, 126 of SEQ ID NO. 1; and
 c) a CD47-binding variant of one of the polypeptide in a) and b) with up to 1 amino acid insertion, deletion or substitution for every 7 amino acids in length of the polypeptide, wherein the polypeptide comprises at least one of residues 31, 32, 34, 37, 74, 77, 83, 84, 86, 87, 90, 91, 96, 100, 102, 114, 118, 126 of SEQ ID NO. 1.

Preferably, the polypeptide is the CD47-binding fragment and comprises at least 3 consecutive amino acids in at least one of a region between residues 50-57, 63-71, 74-80, 88-92, 95-100, 103-109, 114-125 or 128-141, inclusive of SEQ ID NO. 1.

According to another embodiment, the polypeptide capable of modulating the interaction between human Sirpα and human CD47 is selected from the group consisting of:
 a) a polypeptide consisting of the amino acid sequence of SEQ ID NO. 2;
 b) a polypeptide consisting of a CD47-binding fragment of the amino acid sequence of SEQ ID NO. 2; and
 c) a CD47-binding variant of one of the polypeptide in a) and b) with up to 1 amino acid insertion, deletion or substitution for every 7 amino acids in length of the polypeptide;
 wherein:
  i. at least one of residues at positions 31, 32, 34, 37, 74, 77, 83, 84, 86, 87, 90, 91, 96, 100, 102, 114, 118, 126 of SEQ ID NO. 2 in the polypeptide is replaced with corresponding residues 31, 32, 34, 37, 74, 77, 83, 84, 86, 87, 90, 91, 96, 100, 102, 114, 118, 126 of SEQ ID NO. 1; or
  ii. at least one of residues 129 and 130 of SEQ ID NO. 2 in the polypeptide is deleted.

Preferably, the polypeptide is the CD47-binding fragment and comprises at least 3 consecutive amino acids in at least one of a region between residues 50-57, 63-71, 74-80, 88-92, 95-100, 103-109, 114-125 or 128-143, inclusive of SEQ ID NO. 2.

According to another embodiment, the polypeptide capable modulating the interaction between human Sirpα and human CD47 is selected from the group consisting of:
 a) a polypeptide consisting of an amino acid sequence selected from the group consisting of SEQ ID NOS. 4-7;
 b) a polypeptide consisting of a CD47-binding fragment of an amino acid sequence selected from the group consisting of SEQ ID NOS. 4-7; and
 c) a CD47-binding variant of one of the polypeptide in a) and b) with up to 1 amino acid insertion, deletion or substitution for every 7 amino acids in length of the polypeptide.

Preferably, the polypeptide is the CD47-binding fragment and comprises at least 3 consecutive amino acids in at least one of a region between residues 24-31, 37-45, 48-54, 62-66, 69-74, 77-83, 88-99 or 102-116, inclusive, of any one of SEQ ID NOs. 4, 6 and 7; or between residues 24-31, 37-45, 48-54, 62-66, 69-74, 77-83, 88-99 or 102-115, inclusive, of SEQ ID NO. 5.

In some embodiments, the amino acid insertion, deletion or substitution is a conservative amino acid substitution. In other embodiments, there is no amino acid insertion, deletion or substitution.

In some embodiments, the polypeptide is the CD47-binding fragment and is between 6 and 30 amino acids in length, and in increasing preferability, between 8 and 28 amino acids in length, between 10 and 26 amino acids in length, between 12 and 24 amino acids in length, between 14 and 22 amino acids in length.

In some embodiments, the polypeptide is fused to a second polypeptide, preferably the Fc portion of IgG. In one embodiment the polypeptide is a Sirpα-Fc fusion protein, and preferably SEQ ID NO. 13.

According to a further aspect, there is provided a pharmaceutical composition for treating a hematological cancer, preferably leukemia, and further preferably human acute myeloid leukemia (AML), comprising an effective amount of a polypeptide described herein and a pharmaceutically acceptable carrier.

The advantages of the present invention are further illustrated by the following examples. The examples and their particular details set forth herein are presented for illustration only and should not be construed as a limitation on the claims of the present invention.

EXAMPLES

Mice

NOD/LtSz-Prdkc$^{sc/sc}$ (NOD.SCID) (Shultz, L. D. et al. Multiple defects in innate and adaptive immunologic function in NOD/LtSz-scid mice. *J Immunol* 154, 180-191 (1995)) were bred and maintained under sterile conditions at the Ontario Cancer Institute (Toronto, Canada). NOD.NOR-Idd13 mice were maintained in either specific pathogen-free or barrier conditions at the Hospital for Sick Children (Toronto, Ontario).

NOD.NOR-Idd13.SCID mice were generated from an intercross of NOD.NOR-Idd13 mice to NOD.SCID mice, followed by brother-sister matings screened by marker assisted genotyping until homozygosity was achieved at both Idd13 and SCID loci (Takenaka et al., supra).

Transplantation of Human Hematopoietic Cells into Mice

After informed consent was obtained, peripheral blood cells were obtained from patients with primary or secondary AML according to procedures approved by the Human Experimentation Committee. Low-density cells (less than 1.077 g/ml) were collected after separation on Ficoll-Hypaque (Pharmacia, Piscataway, N.J.) and then cryopreserved in FCS containing 10% dimethyl sulfoxide.

8- to 10-week-old mice were sublethally irradiated with 275 cGy from a $^{137}$Cs γ-irradiator 24 hours before transplantation of human cells. Mice were sacrificed 7-8 weeks post-transplantation, and murine BM and spleen was assessed for human cell engraftment by flow cytometric analysis for the presence of human CD45$^+$ cells. In mice transplanted intrafemorally, the injected femur and the remaining bones (non-injected femur, tibias) were analyzed separately. In some experiments, mice were pretreated with 200 μg of anti-murine CD122 intraperitoneally after irradiation.

Flow Cytometry

A LSR II (BD) was used for flow cytometry. For analysis of human cell engraftment in mice, cells collected from mouse bone marrow were stained with phycoerythrin-Cy7-conjugated anti-human CD45 (HI.30; BD Pharmingen).

Human SIRP V1 and V2 Cloning into Type I TM Vector

Human SIRPα Variant 1 and 2 cDNA in pUC57 plasmid was PCR amplified in 5× HF Buffer using XhoI containing forward primer, BglII containing reverse primer and Phusion Hot start II High fidelity polymerase in order to obtain the complete IgV domain of SIRPα variant 1 and 2.

pUC57 SIRPα vector were subjected to restriction digest with XhoI and BglII. pINFUSE-hIgG4-Fc1 was digested with EcoRI and BglII and the SIRPα insert was ligated into pINFUSE-hIgG4-Fc1 using LigaFast Rapid DNA ligation System from Promega™.

The resulting pINFUSE-hIgG4-Fc1-human SIRPα vector was transformed into One Shot TOP10 competent *E.coli* from Invitrogen.

Transfection

Plasmid DNA and fectin were diluted in an appropriate volume of OptiMeM and mixed. FreeStyle™ 293-F cells were transfected at 37° C. incubator with a humidified atmosphere of 8% $CO^2$ in air. Cells or media was were harvested 4 to 6 days after transfection.

Protein Harvest

Fc protein was harvested from 293F culture. The culture was spun and the supernatant collected and filtered through a PES 0.45 um filter, then through a PES 0.22 um filter. The supernatant was concentrated using Centricon-70 mL centrifugation filters at ~3500×g for 10-20 mins and eluted in a G column at 4° C. The protein was collected in 1M Tris HCl pH 8.0. The sample was further desalted by centrifugation and resuspended in PBS.

Example 1

To investigate the relevance of CD47-SIRPα interaction in primary human AMLs, we transplanted primary cells from three AML patients intravenously (i.v.) into NOD-.SCID and NOD.NOR-Idd13.SCID (Idd) mice. None of the AML samples could engraft the Idd mice while robust engraftment in the NOD.SCID mice was observed (FIG. 1), confirming the data obtained previously with normal human HSCs. When the same samples were transplanted intrafemorally (i.f.), 2 of 6 Idd mice showed engraftment in the injected femur but no engraftment in other bones or the spleen (FIG. 1).

Example 2

Figure 2:
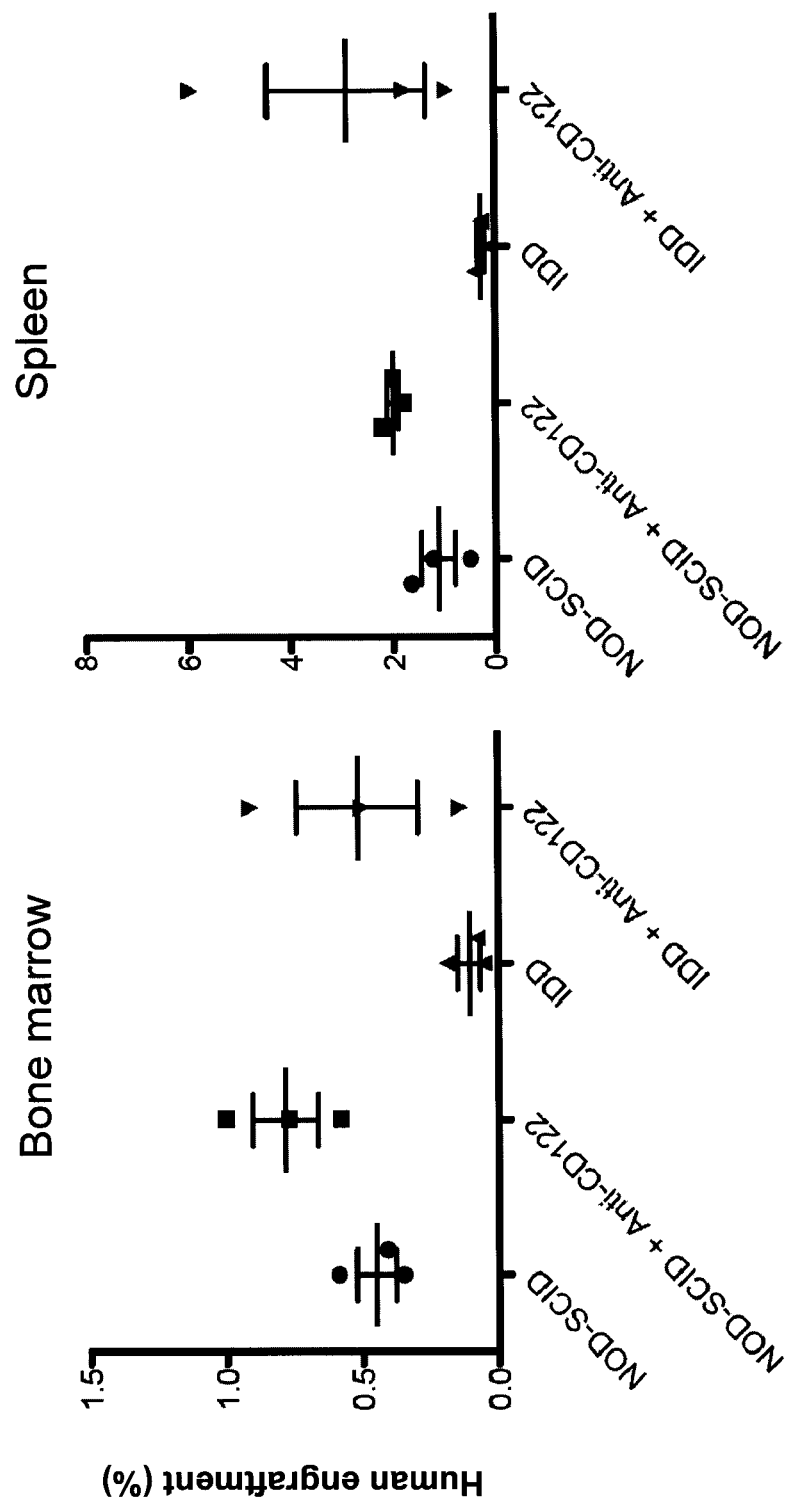
FIG. 2(A) shows defective homing of AML cells in NOD.NOR-Idd13.SCID mice. Percentage of human CD45+ engraftment in BM or spleen of sublethally irradiated NOD.SCID and NOD.NOR-Idd13.SCID (IDD) mice 16 hours after i.v. injection of primary AML cells, determined by flow cytometry. Each dot, square or triangle represents a single mouse. Bars indicate mean±SEM.
FIG. 2(B) shows AML-LSC function is held in check by innate immune cells. Primary cells from 10 AML patients with different leukemia subtypes and cytogenetic markers were transplanted i.f. into NOD.SCID or NOD.NOR-Idd13.SCID (IDD) mice pretreated with anti-murine CD122 antibody. The percentage of human engraftment in the injected right femur (RF), marrow from non-injected bones (BM) or spleen (SP) was determined 7-8 weeks later (Y axis). Compared to untreated mice (FIG. 1), repression of leukemic engraftment in IDD mice is reduced by pretreatment with anti-CD122.
Figure 2:
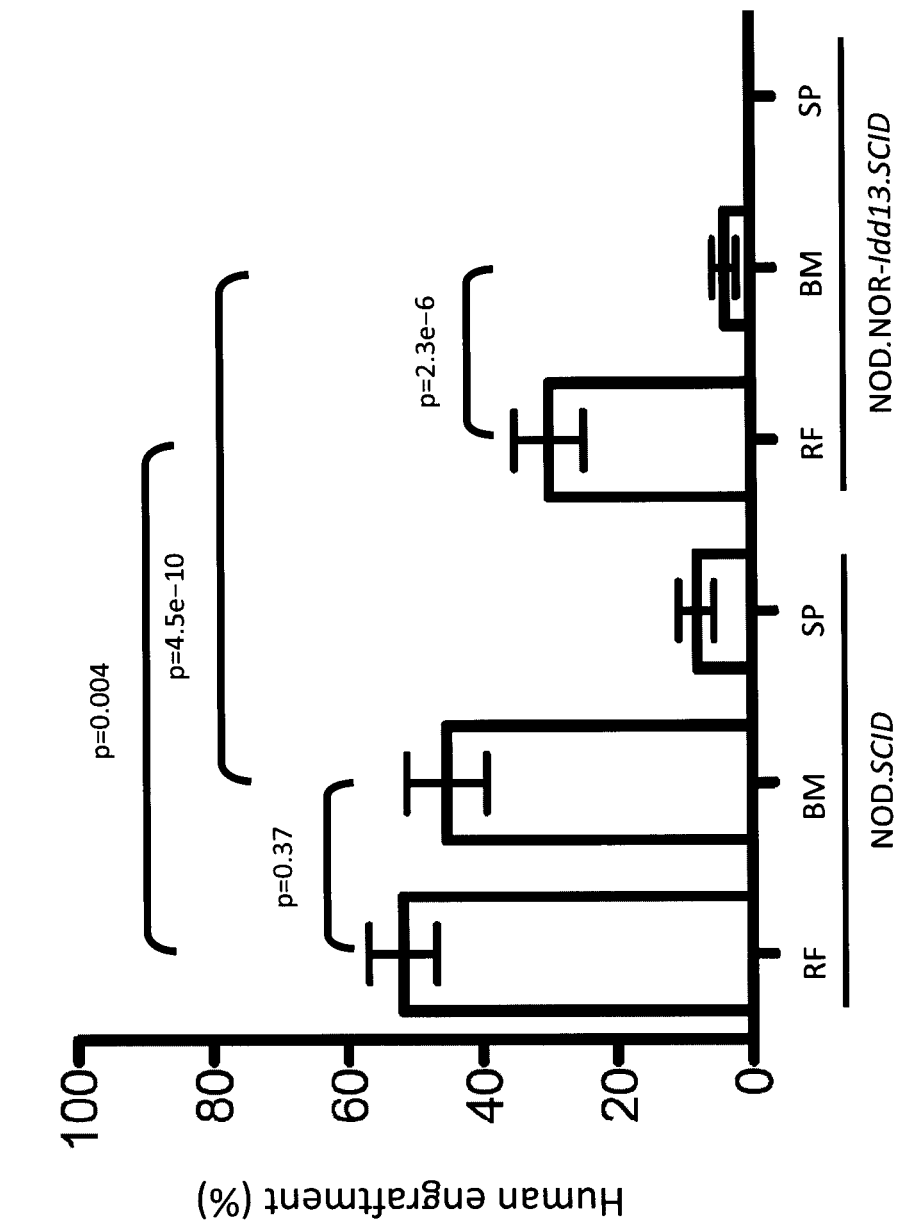

We next performed i.f. transplants into mice pre-treated with antibody directed against murine CD122 which depletes host natural killer (NK) cells and some macrophages. Engraftment in the injected femur was observed for all 10 AML samples tested in NOD.SCID mice (43/43, 100%), and interestingly in 31 of 42 (74%) Idd mice (8/10 AML samples tested) (FIG. 2B), however the engraftment level was lower in Idd mice compared to NOD.SCID mice. In contrast to results obtained without anti-CD122 pre-treatment, engraftment in non-injected bones was detectable in 8/42 Idd mice (19%, 2/10 AML samples tested) while as expected most of the transplanted NOD.SCID mice supported migration (38/43, 88%, 10/10 AML samples tested). However the engraftment level in non-injected bones was significantly lower in Idd compared to NOD.SCID mice. Moreover, AML-LSCs were unable to repopulate the spleens of Idd mice. Homing assays performed with the best engrafting AML sample in this study revealed severe homing deficiencies in Idd compared to NOD.SCID mice (FIG. 2A).

Example 3

Figure 3:
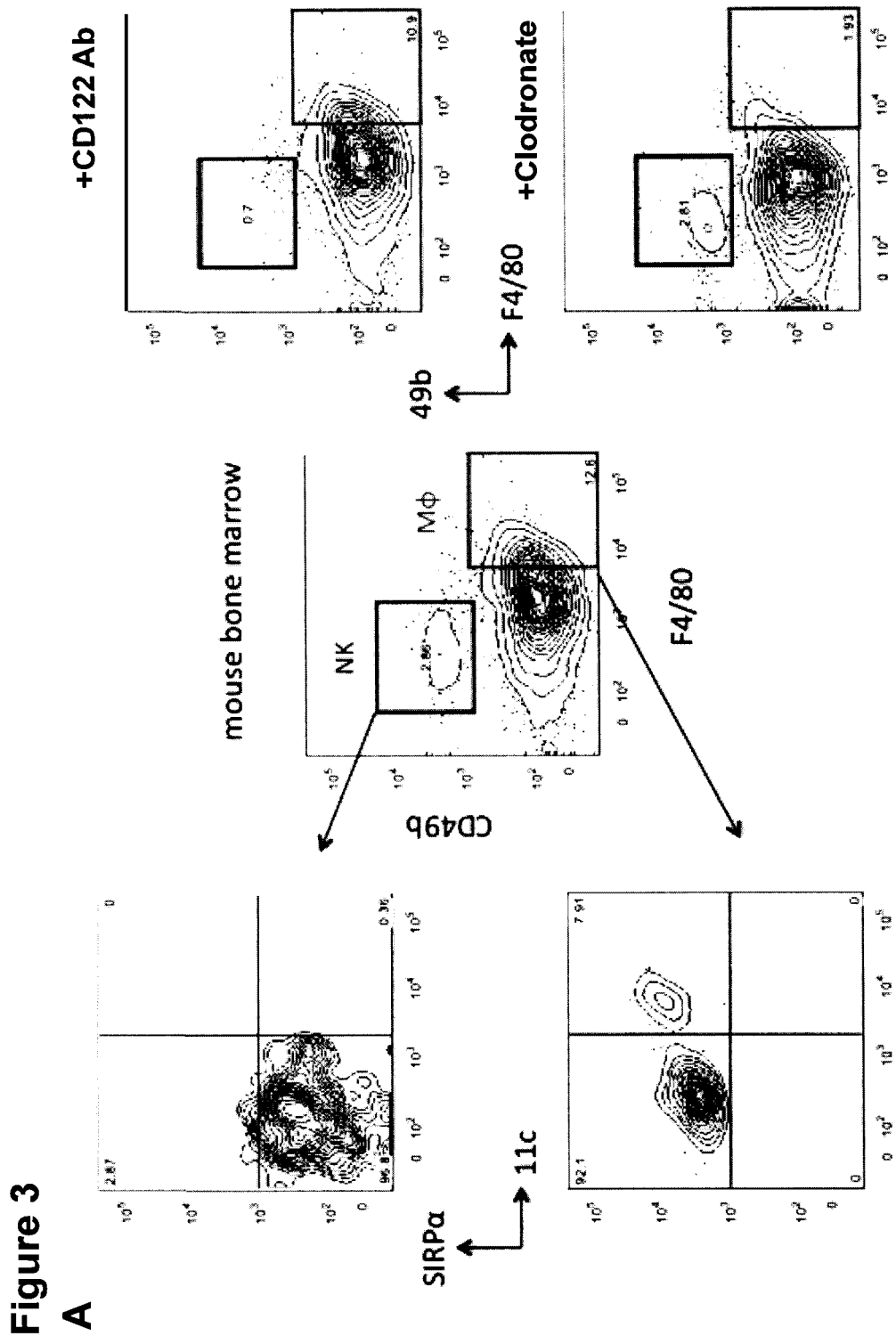
FIG. 3 shows the effect of mouse innate immunity on engraftment of human acute myeloid leukemia (AML) in mouse xenograft. A) Modulation of natural killer (NK) cell and macrophage (Mϕ) populations in NOD.SCID or NOD.NOR-Idd13.SCID. Surface phenotype of mouse NK cells and macrophages are indicated. B) Engraftment of human AML cells in NOD.SCID or NOD.NOR-Idd13.SC/D (Idd) after macrophage depletion. Figures show percentage of human leukemic cells in harvested organs.
Figure 3:
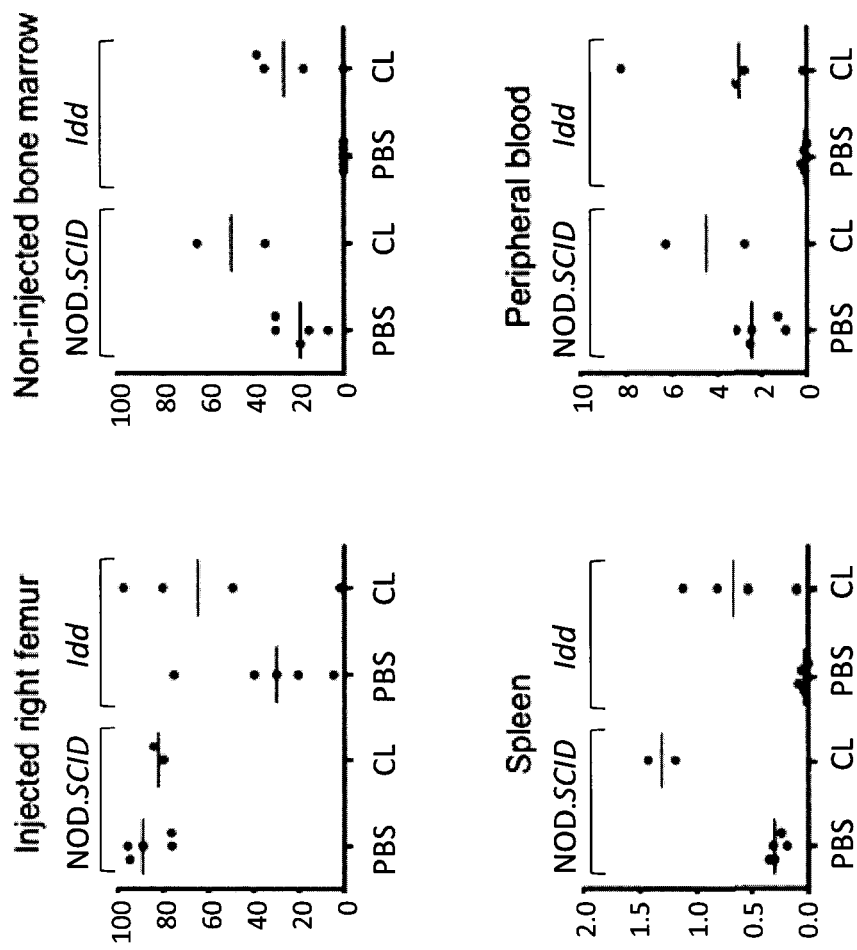

We studied the effect of mouse innate immunity on engraftment of human acute myeloid leukemia (AML) in mouse xenograft. FIG. 3A shows the modulation of natural killer (NK) cell and macrophage (Mφ) populations in NOD.SCID or NOD.NOR-Idd13.SCID. Surface phenotype of mouse NK cells and macrophages are indicated. Macrophages but not NK cells express Sirpα (left panels). Mice were treated with intraperitoneal (i.p.) injections of antibody against CD122 (expressed mainly on NK cells) or Clodronate. CD122 antibody treatment, which has been shown to improve engraftment of human hematopoietic cells in NOD-.SCID mice, leads to rapid NK cell depletion but does not reduce mouse macrophages (upper right panel). Treatment with the bisphosphonate Clodronate leads to apoptosis and efficient depletion of macrophages (lower right panel of FIG. 3A).

FIG. 3B shows the engraftment of human AML cells in NOD.SCID or NOD.NOR-Idd13.SCID (Idd) after macrophage depletion. Sublethally irradiated mice were treated with PBS (controls) or Clodronate (CL) i.p. 48 hours prior to intrafemoral transplantation of human AML cells. Clodronate treatment was continued on a weekly basis until mice were sacrificed 8 weeks after transplantation. Injected bone marrow, non-injected bone marrow, spleen and peripheral blood of mice were harvested and human leukemic engraftment was assessed by flow cytometry using human specific markers. Figures show percentage of human leukemic cells in harvested organs. There is reduced engraftment in the injected femur of PBS-treated control Idd mice compared to NOD.SCID mice and no engraftment at other sites; engraftment at all sites in Idd mice was observed after Clodronate treatment. These findings support the hypothesis that SIRPα-CD47 interactions are critical for AML engraftment, and that decreased engraftment of AML cells in Idd mice is mediated by macrophages.

Example 4

Figure 4:
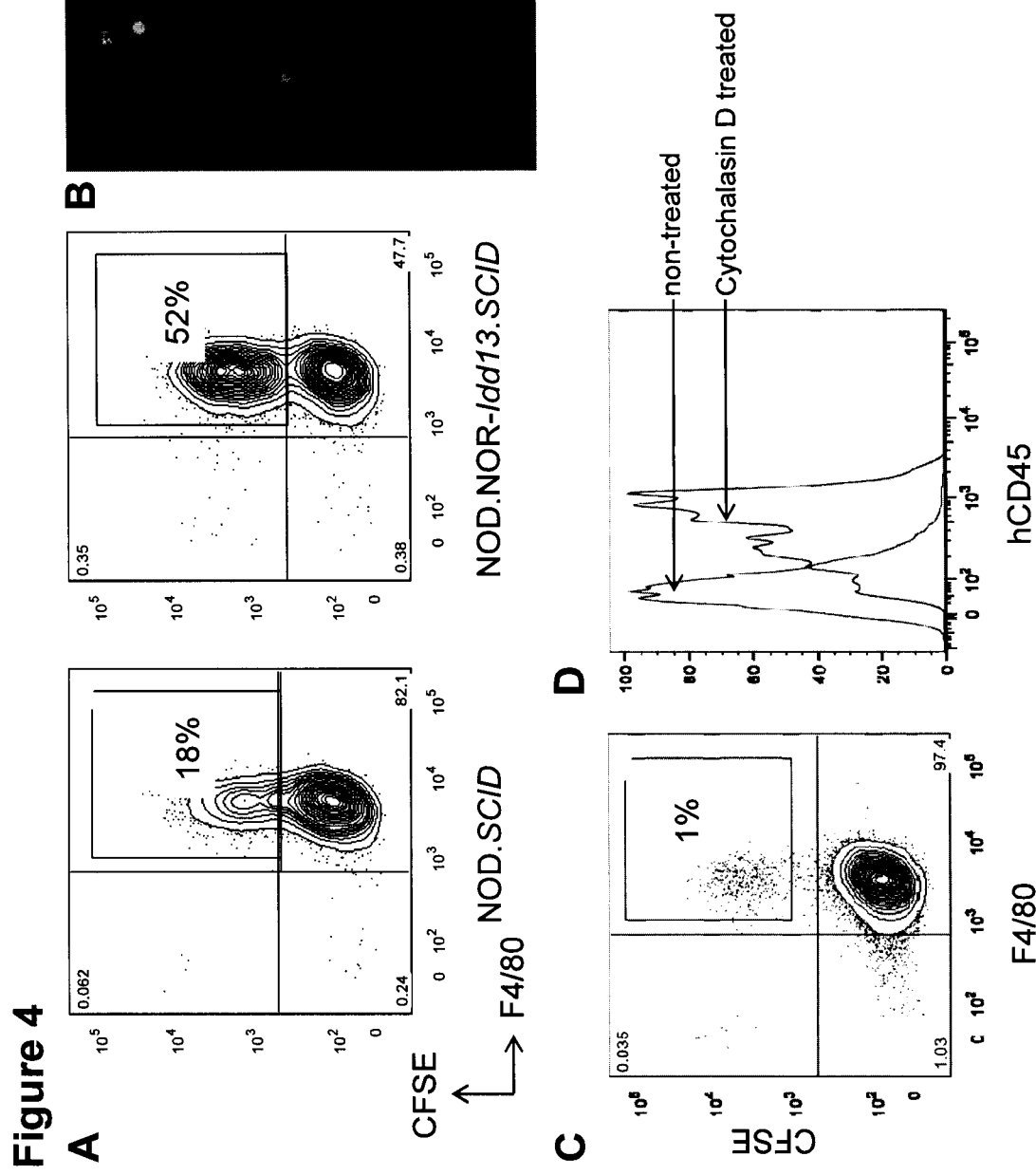
FIG. 4 shows in vitro phagocytosis assay for human AML cells. A) CFSE-labeled human AML cells were co-incubated with NOD.SCID or NOD.NOR-Idd13.SCID mouse macrophages. After 2 hours macrophages were harvested and the percentage of F4/80+ mouse macrophages positive for CFSE was determined by flow cytometry. B) CFSE+/F4/80+ cells were sorted by fluorescent activated cell sorting and visualized using confocal microscopy. C) Co-cultures were pretreated with Cytochalasin D, which inhibits phagocytosis by inhibiting actin polymerization in macrophages. D) Expression of human CD45 in untreated or Cytochalasin D treated CFSE+/F4/80+ mouse macrophages, as indicated.

In vitro phagocytosis assay for human AML cells was performed. CFSE-labeled human AML cells were co-incubated with NOD.SCID or NOD.NOR-Idd13.SCID mouse macrophages. After 2 hours macrophages were harvested and the percentage of F4/80+ mouse macrophages positive for CFSE was determined by flow cytometry. CFSE-positivity of mouse macrophages suggests engulfment of human CFSE+ AML cells (FIG. 4A). NOD.NOR-Idd13.SCID-AML co-cultures consistently showed higher percentages of CFSE+/F4/80+ compared to NOD.SCID-AML co-cultures. This suggests that the lack of interaction between CD47 on AML cells and Sirpα on mouse macrophages results in increased phagocytosis of AML cells.

Following fluorescent activated cell sorting, CFSE+/F4/80+ cells were visualized using confocal microscopy. FIG. 4B shows one informative field with CFSE+ cells engulfed by macrophages.

Co-cultures were pretreated with Cytochalasin D, which inhibits phagocytosis by inhibiting actin polymerization in macrophages. Cytochalasin D treatment significantly reduced the percentage of CFSE+/F4/80+ cells (FIG. 4C).

FIG. 4D shows the expression of human CD45 in untreated or Cytochalasin D treated CFSE+/F4/80+ mouse macrophages, as indicated. Low expression of human CD45 suggests engulfment of human AML cells in mouse macrophages as human antibodies are unable to bind to engulfed cells. These results confirm that the majority of untreated CFSE+/F4/80+ cells are macrophages that have ingested human AML cells (CD45 negative). Overall, these findings suggest that SIRPα-CD47 interactions are critical for AML cells to evade innate immune attack by macrophages.

Example 5

Example 5 demonstrates that in vitro pre-incubation of human SIRPα (V2) fusion protein blocks homing of primary AML cells into NOD.SCID mouse bone marrow (BM) and spleen. Primary cells harvested from AML Pt9601 were incubated with or without human SIRPα-Fc fusion protein at a concentration of 50 µg/ml in IMDM+15% BIT for 2 hours at 37° C. Cells incubated with (hSIRPα-Fc) or without (No treatment) fusion protein were harvested and transplanted intravenously into sublethally irradiated NOD.SCID mice. Sixteen hours post transplantation, mice were sacrificed and cells were harvested from BM and spleen.

The percentage of human CD44+ AML cells in BM and spleen was measured by flow cytometry using murine anti-human antibodies. In vitro incubation with human SIRPα-Fc significantly decreased the percentage of human CD44+ AML cells in both BM (P=0.02) and spleen (P=0.018), compared to the untreated group (FIG. 5A—each symbol represents a different mouse).

Homing efficiency of AML cells to NOD.SCID BM and spleen was calculated as [Total #AML cells recovered]/[Total #AML cells injected]×100. Human SIRPα-Fc treatment significantly reduced the homing efficiency of AML cells to NOD.SCID BM (P=0.036) and also to spleen (NS) (FIG. 5B).

Example 6

Figure 6:
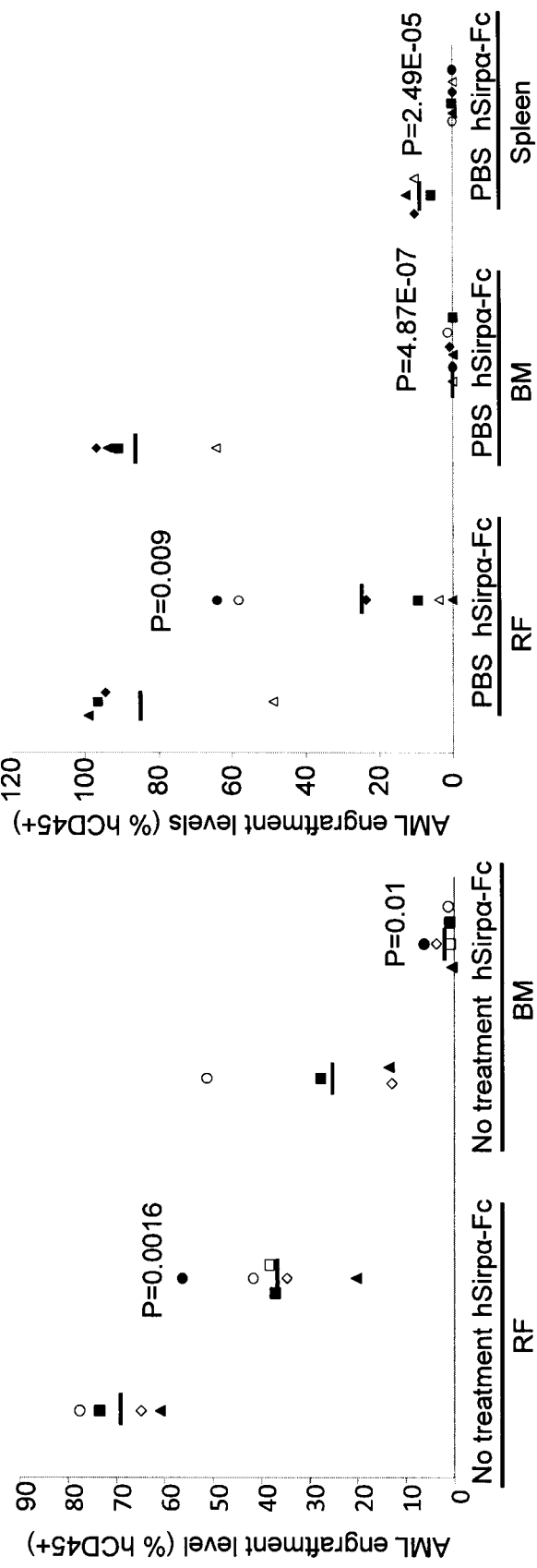
FIG. 6 shows that in vitro treatment with human Sirpα fusion protein (hSirpα-Fc) decreases the repopulating ability of primary AML cells in NOD.SCID mice. Bars indicate the mean percentage of hCD45+ cells.

Example 6 shows that in vitro treatment with human Sirpα fusion protein (hSirpα-Fc) decreases the repopulating ability of primary AML cells in NOD.SCID mice. Primary AML cells from Pt90181 (unclassified AML) were incubated with or without hSirpα-Fc at a concentration of 50 µg/ml in IMDM+15% BIT for 2 hours at 37° C. After incubation, cells were harvested and transplanted intrafemorally into sublethally irradiated NOD.SCID mice at $2.7\times10^6$ cells per mouse. 4 weeks post transplantation, mice were sacrificed and cells were harvested from the injected femur (RF) and uninjected femur (BM) for staining with anti-human antibodies. Stained cells were analyzed by flow cytometry to determine the engraftment levels in each individual mouse based on the percentage of hCD45+ cells (FIG. 6). Bars indicate the mean percentage of hCD45+ cells. Pre-incubation of AML cells with hSirpα-Fc significantly decreased AML engraftment levels in both RF (P=0.0016) and BM (P=0.01) compared to untreated controls.

Example 7

Figure 7:
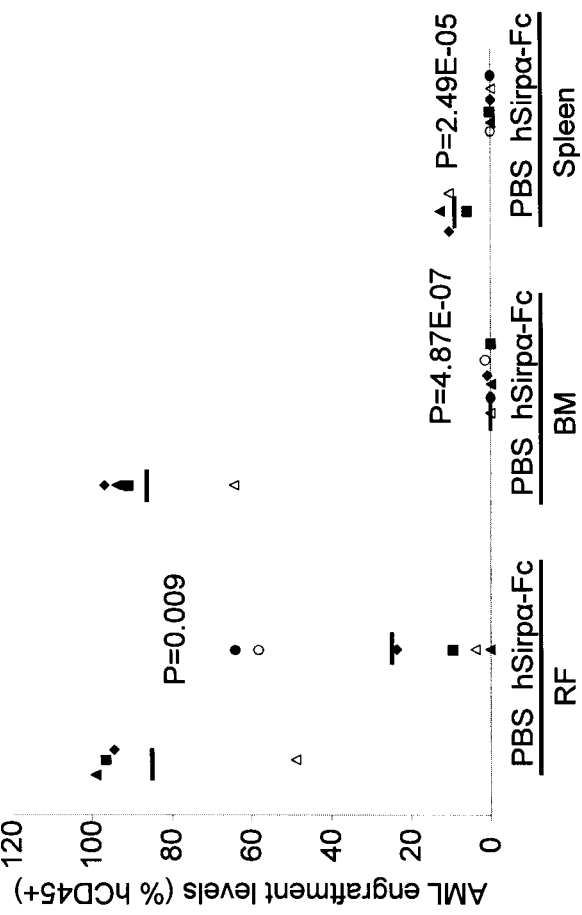
FIG. 7 shows that in vivo human Sirpα fusion protein (hSirpα-Fc) treatment decreases engraftment of primary AML cells in NOD.SCID mice. Stained cells were analyzed by flow cytometry to determine the engraftment levels in each mouse based on the percentage of hCD45+ cells. Bars indicate the average percentage of hCD45+ human cells in each group. Indicated P values are for hSirpα-Fc treatment compared to PBS-treatment.

Example 7 demonstrates that in vivo human Sirpα fusion protein (hSirpα-Fc) treatment decreases engraftment of primary AML cells in NOD.SCID mice. Primary AML cells from patient 0285 (FAB M2) were injected intrafemorally into sublethally irradiated NOD.SCID mice. Starting 10 days post transplantation, hSirpα-Fc was administered intraperitoneally at a dose of 200 µg per mouse (8 mg/kg), 3 times/week for 7 doses. Mice were then sacrificed and cells harvested from the injected femur (RF), uninjected femur (BM) and spleen for staining with anti-human antibodies. Stained cells were analyzed by flow cytometry to determine the engraftment levels in each mouse based on the percentage of hCD45+ cells (FIG. 7). Bars indicate the average percentage of hCD45+ human cells in each group. Indicated P values are for hSirpα-Fc treatment compared to PBS-treatment. Treatment with hSirpα-Fc dramatically decreased AML engraftment levels in all tissues analyzed. Profound reduction of AML cells in BM and spleen to almost undetectable levels suggests that hSirpα-Fc completely inhibited AML stem cell migration from the injected femur to other hematopoietic sites.

Discussion

Here we have shown that human AML-LSC have significantly reduced engraftment ability in NOD.NOR-Idd13.SCID mice, in concordance with the data obtained with normal hematopoietic cells. Our results are consistent with those obtained with anti-CD47 treatment of mice engrafted with AML (Majeti et al., supra), and support the hypothesis that attenuation of CD47-SIRPα interaction (as in Idd mice) impairs AML-LSC function. This effect is somewhat ameliorated by depletion of NK cells and macrophages through anti-CD122 treatment, enabling engraftment in the injected femur and in some cases migration to other bones. This suggests that at least some of the anti-leukemic activity in vivo may be mediated by cells of the innate immune system, in particular macrophages expressing SIRPα. Our findings further suggest that SIRPα-CD47 interactions are critical for AML cells to evade innate immune attack by macrophages. Interruption of CD47-SIRPα signaling through targeting of either CD47 or SIRPα is a therapeutic approach for eradication of hematological cancers cells such as leukemic stem cells, preferably AML-LSC. We demonstrate that human SIRPα (V2) fusion protein blocks homing of primary AML cells into NOD.SCID mouse bone marrow (BM) and spleen and decreases the repopulating ability of primary AML cells in NOD.SCID mice. Notably, we demonstrate that in vivo human Sirpα fusion protein (hSirpα-Fc) treatment decreases engraftment of primary AML cells in NOD.SCID mice.

Although preferred embodiments of the invention have been described herein, it will be understood by those skilled in the art that variations may be made thereto without departing from the spirit of the invention or the scope of the appended claims. All documents disclosed herein are incorporated by reference.

The invention claimed is:

1. A method for treating a patient having cancer cells or tumours that are CD47±, comprising administering to the patient a therapeutically effective amount of a fusion protein capable of binding to the extracellular domain of human CD47 to interrupt signaling between human Sirpα and human CD47, wherein the fusion protein comprises a first polypeptide comprising soluble human Sirpα, or a CD47 binding fragment thereof, fused to a second polypeptide comprising the Fc portion of IgG, and wherein the method results in a desuppression of macrophages.

2. The method of claim 1, wherein the first polypeptide comprises a CD47 binding fragment of soluble human Sirpα.

3. The method of claim 2, wherein the first polypeptide comprises the extracellular domain of human Sirpα.

4. The method of claim 2, wherein the fusion protein comprises a member selected from the group consisting of, human Sirpa-Fc, human Sirpa (extracellular domain)-Fc, IgV domain of human Sirpa-Fc, IgV domain of human Sirpa (variant 1)-Fc, and IgV domain of human Sirpa(variant 2)-Fc.

5. The method of claim 1, wherein the first polypeptide is selected from the group consisting of:
   a. a polypeptide consisting of an amino acid sequence selected from the group consisting of SEQ ID NOs: 4-7; and
   b. a polypeptide consisting of a CD47-binding fragment of an amino acid sequence selected from the group consisting of SEQ ID NOs: 4-7.

6. The method of claim 1, wherein the first polypeptide comprises a CD47 binding fragment of the extracellular domain of human Sirpa.

7. The method of claim 1, wherein the first polypeptide comprises the IgV domain of human Sirpa.

8. The method of claim 1, wherein the first polypeptide comprises the IgV domain of human Sirpa variant 1.

9. The method of claim 1, wherein the first polypeptide comprises the IgV domain of human Sirpa variant 2.

10. The method of claim 2, wherein the second polypeptide comprises the Fc portion of human IgG1.

11. The method of claim 2, wherein the second polypeptide comprises the Fc portion of human IgG4.

12. The method of claim 4, wherein Fc is the Fc portion of human IgG1 or human IgG4.

13. The method of claim 1, wherein the first polypeptide comprises an amino acid sequence selected from the group consisting of SEQ ID NOs: 4-7;
and CD47-binding fragments of SEQ ID NOs: 4-7.

14. The method according to claim 1 that comprises administering to the patient a composition that comprises the fusion protein and a pharmaceutically acceptable carrier.

15. A method for treating a patient having a hematological cancer that expresses CD47, the method comprising
   administering to the patient a therapeutically effective amount of a fusion protein capable of binding to the extracellular domain of human CD47 and interrupting CD47-SIRPα signaling,
   wherein the fusion protein comprises a first polypeptide comprising a soluble human Sirpa, or a CD47 binding fragment thereof, fused to a second polypeptide comprising a Fc portion of IgG.

16. The method of claim 15, wherein the hematological cancer is leukemia.

17. The method of claim 16, wherein the leukemia is human acute myeloid leukemia.

18. The method of claim 15, wherein the hematological cancer is a lymphoma or myeloma selected from Hodgkin's lymphoma, indolent non-Hodgkin's lymphoma, aggressive non-Hodgkin's lymphoma, Burkitt's lymphoma, small cell follicular lymphoma, large cell follicular lymphoma, multiple myeloma (MM), giant cell myeloma, heavy-chain myeloma, and light chain or Bence-Jones myeloma.

19. The method of claim 16, wherein the leukemia is selected from acute lymphocytic leukemia, chronic myelogenous leukemia, myeloproliferative disorder/neoplasm and myelodysplastic syndrome.

20. The method of claim 16, wherein the leukemia is chronic lymphocytic leukemia.

21. The method of claim 15, wherein the first polypeptide comprises a CD47 binding fragment of soluble human Sirpa.

22. The method of claim 21, wherein the first polypeptide comprises an IgV domain of human Sirpa.

23. The method of claim 22, wherein the first polypeptide comprises the IgV domain of human Sirpa variant 1.

24. The method of claim 22, wherein the first polypeptide comprises the IgV domain of human Sirpa variant 2.

25. The method of claim 21, wherein the first polypeptide comprises the extracellular domain of human Sirpa.

26. The method of claim 15, wherein the first polypeptide comprises an amino acid sequence selected from the group consisting of SEQ ID NOs: 4-7;
and CD47-binding fragments of SEQ ID NOs: 4-7.

27. The method of claim 15, wherein the second polypeptide comprises the Fc portion of human IgG1.

28. The method of claim 15, wherein the second polypeptide comprises the Fc portion of human IgG4.

29. The method of claim 22, wherein Fc is the Fc portion of human IgG1 or human IgG4.

30. The method according to claim 15 that comprises administering to the patient a composition that comprises the fusion protein and a pharmaceutically acceptable carrier.

31. A method of desuppressing macrophages, to treat a patient with a tumor or a hematological cancer that expresses CD47, the method comprising
   administering to the patient a therapeutically effective amount of a fusion protein that is capable of binding to the extracellular domain of human CD47 and interrupting CD47-SIRPα signaling,
   wherein the fusion protein comprises a first polypeptide comprising a soluble human Sirpα, or a CD47 binding fragment thereof, fused to a second polypeptide comprising a Fc portion of IgG.

32. The method of claim 31, wherein the first polypeptide comprises a CD47 binding fragment of soluble human Sirpa.

33. The method of claim 32, wherein the first polypeptide comprises the extracellular domain of human Sirpa.

34. The method of claim 32, wherein the first polypeptide comprises an IgV domain of human Sirpa.

35. The method of claim 34, wherein the first polypeptide comprises the IgV domain of human Sirpa variant 1.

36. The method of claim 34, wherein the first polypeptide comprises the IgV domain of human Sirpa variant 2.

37. The method of claim 34, wherein Fc is the Fc portion of human IgG1 or human IgG4.

38. The method of claim 31, wherein the first polypeptide comprises an amino acid sequence selected from the group consisting of SEQ ID NOs: 4-7;
and CD47-binding fragments of SEQ ID NOs: 4-7.

39. The method of claim 31, wherein the second polypeptide comprises the Fc portion of human IgG1.

40. The method of claim 31, wherein the second polypeptide comprises the Fc portion of human IgG4.

41. The method according to claim 31 that comprises administering to the patient a composition that comprises the fusion protein and a pharmaceutically acceptable carrier.

42. The method according to claim 31, wherein the tumor or a hematological cancer that expresses CD47 has been identified using a CD47 antibody.

* * * * *

SEQUENCE LISTING

<160> NUMBER OF SEQ ID NOS: 13

<210> SEQ ID NO 1
<211> LENGTH: 507
<212> TYPE: PRT
<213> ORGANISM: mouse

<400> SEQUENCE: 1

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Arg Thr
            20                  25                  30

Glu Val Lys Val Ile Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Gln Ser Arg Gln Leu Ile Tyr
65                  70                  75                  80

Ser Phe Thr Thr Glu His Phe Pro Arg Val Thr Asn Val Ser Asp Ala
                85                  90                  95

Thr Lys Arg Ser Asn Leu Asp Phe Ser Ile Arg Ile Ser Asn Val Thr
            100                 105                 110

Pro Glu Asp Ala Gly Thr Tyr Tyr Cys Val Lys Phe Gln Arg Gly Ser
        115                 120                 125

Pro Asp Thr Glu Ile Gln Ser Gly Gly Gly Thr Glu Val Tyr Val Leu
    130                 135                 140

Ala Lys Pro Ser Pro Pro Glu Val Ser Gly Pro Ala Asp Arg Gly Ile
145                 150                 155                 160

Pro Asp Gln Lys Val Asn Phe Thr Cys Lys Ser His Gly Phe Ser Pro
                165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
        195                 200                 205

Ser Ser Thr Val Arg Val Val Leu Asn Ser Met Asp Val His Ser Lys
    210                 215                 220

-continued

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
            245                 250                 255

Val Thr Gln Gln Ser Pro Thr Ser Met Ser Gln Val Asn Leu Thr Cys
            260                 265                 270

Arg Ala Glu Arg Phe Tyr Pro Glu Asp Leu Gln Leu Ile Trp Leu Glu
            275                 280                 285

Asn Gly Asn Val Ser Arg Asn Asp Thr Pro Lys Asn Leu Thr Lys Asn
            290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
            325                 330                 335

Gln Pro Ala Ile Thr Arg Asn His Thr Val Leu Gly Leu Ala His Ser
            340                 345                 350

Ser Asp Gln Gly Ser Met Gln Thr Phe Pro Gly Asn Asn Ala Thr His
            355                 360                 365

Asn Trp Asn Val Phe Ile Gly Val Gly Val Ala Cys Ala Leu Leu Val
370                 375                 380

Val Leu Leu Met Ala Ala Leu Tyr Leu Leu Arg Ile Lys Gln Lys Lys
385                 390                 395                 400

Ala Lys Gly Ser Thr Ser Ser Thr Arg Leu His Glu Pro Glu Lys Asn
            405                 410                 415

Ala Arg Glu Ile Thr Gln Ile Gln Asp Thr Asn Asp Ile Asn Asp Ile
            420                 425                 430

Thr Tyr Ala Asp Leu Asn Leu Pro Lys Glu Lys Lys Pro Ala Pro Arg
            435                 440                 445

Ala Pro Glu Pro Asn Asn His Thr Glu Tyr Ala Ser Ile Glu Thr Gly
            450                 455                 460

Lys Val Pro Arg Pro Glu Asp Thr Leu Thr Tyr Ala Asp Leu Asp Met
465                 470                 475                 480

Val His Leu Ser Arg Ala Gln Pro Ala Pro Lys Pro Glu Pro Ser Phe
            485                 490                 495

Ser Glu Tyr Ala Ser Val Gln Val Gln Arg Lys
            500                 505

<210> SEQ ID NO 2
<211> LENGTH: 509
<212> TYPE: PRT
<213> ORGANISM: mouse

<400> SEQUENCE: 2

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
            35                  40                  45

Asp Ser Thr Val Leu Asn Cys Thr Leu Thr Ser Leu Leu Pro Val Gly
            50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
            85                  90                  95

-continued

```
Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
            115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
        435                 440                 445

Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505
```

<210> SEQ ID NO 3
<211> LENGTH: 513
<212> TYPE: PRT
<213> ORGANISM: mouse

<400> SEQUENCE: 3

Met Glu Pro Ala Gly Pro Ala Pro Gly Arg Leu Gly Pro Leu Leu Leu
1               5                   10                  15

Cys Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Met Ala Ala Leu Tyr Leu Arg Ile Lys Gln
385                 390                 395                 400

Lys Lys Ala Lys Gly Ser Thr Ser Thr Arg Leu His Glu Pro Glu
                405                 410                 415

Lys Asn Ala Arg Glu Ile Thr Gln Val Gln Ser Leu Ile Gln Asp Thr
                420                 425                 430

Asn Asp Ile Asn Asp Ile Thr Tyr Ala Asp Leu Asn Leu Pro Lys Glu
                435                 440                 445

Lys Lys Pro Ala Pro Arg Ala Pro Glu Pro Asn Asn His Thr Glu Tyr
                450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
                500                 505                 510

Lys

<210> SEQ ID NO 4
<211> LENGTH: 120
<212> TYPE: PRT
<213> ORGANISM: human

<400> SEQUENCE: 4

Gly Val Ala Gly Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
                20                  25                  30

Ser Leu Ile Pro Val Gly Pro Ile Gln Trp Phe Arg Gly Ala Gly Pro
            35                  40                  45

Gly Arg Glu Leu Ile Tyr Asn Gln Lys Glu Gly His Phe Pro Arg Val
        50                  55                  60

Thr Thr Val Ser Asp Leu Thr Lys Arg Asn Asn Met Asp Phe Ser Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Val Glu Phe Lys Ser Gly Ala
            100                 105                 110

Gly Thr Glu Leu Ser Val Arg Ala
        115                 120

<210> SEQ ID NO 5
<211> LENGTH: 119
<212> TYPE: PRT
<213> ORGANISM: human

<400> SEQUENCE: 5

Gly Val Ala Gly Glu Glu Leu Gln Val Ile Gln Pro Asp Lys Ser
1               5                   10                  15

Val Ser Val Ala Ala Gly Glu Ser Ala Ile Leu His Cys Thr Val Thr
                20                  25                  30

Ser Leu Ile Pro Val Gly Pro Ile Gln Trp Phe Arg Gly Ala Gly Pro
            35                  40                  45

Ala Arg Glu Leu Ile Tyr Asn Gln Lys Glu Gly His Phe Pro Arg Val
        50                  55                  60

```
Thr Thr Val Ser Glu Ser Thr Lys Arg Glu Asn Met Asp Phe Ser Ile
 65                  70                  75                  80

Ser Ile Ser Asn Ile Thr Pro Ala Asp Ala Gly Thr Tyr Tyr Cys Val
                 85                  90                  95

Lys Phe Arg Lys Gly Ser Pro Asp Thr Glu Phe Lys Ser Gly Ala Gly
            100                 105                 110

Thr Glu Leu Ser Val Arg Ala
            115
```

<210> SEQ ID NO 6
<211> LENGTH: 120
<212> TYPE: PRT
<213> ORGANISM: human

<400> SEQUENCE: 6

```
Gly Val Ala Gly Glu Glu Leu Gln Val Ile Gln Pro Asp Lys Ser
  1               5                  10                  15

Val Ser Val Ala Ala Gly Glu Ser Ala Ile Leu His Cys Thr Val Thr
                 20                  25                  30

Ser Leu Ile Pro Val Gly Pro Ile Gln Trp Phe Arg Gly Ala Gly Pro
                 35                  40                  45

Ala Arg Glu Leu Ile Tyr Asn Gln Lys Glu Gly His Phe Pro Arg Val
 50                  55                  60

Thr Thr Val Ser Glu Ser Thr Lys Arg Glu Asn Met Asp Phe Ser Ile
 65                  70                  75                  80

Ser Ile Ser Asn Ile Thr Pro Ala Asp Ala Gly Thr Tyr Tyr Cys Val
                 85                  90                  95

Lys Phe Arg Lys Gly Ser Pro Asp Asp Val Glu Phe Lys Ser Gly Ala
            100                 105                 110

Gly Thr Glu Leu Ser Val Arg Ala
            115                 120
```

<210> SEQ ID NO 7
<211> LENGTH: 120
<212> TYPE: PRT
<213> ORGANISM: human

<400> SEQUENCE: 7

```
Gly Val Ala Gly Glu Glu Leu Gln Val Ile Gln Pro Asp Lys Ser
  1               5                  10                  15

Val Leu Val Ala Ala Gly Glu Thr Ala Thr Leu Arg Cys Thr Ala Thr
                 20                  25                  30

Ser Leu Ile Pro Val Gly Pro Ile Gln Trp Phe Arg Gly Ala Gly Pro
                 35                  40                  45

Gly Arg Glu Leu Ile Tyr Asn Gln Lys Glu Gly His Phe Pro Arg Val
 50                  55                  60

Thr Thr Val Ser Asp Leu Thr Lys Arg Asn Asn Met Asp Phe Ser Ile
 65                  70                  75                  80

Arg Ile Ser Asn Ile Thr Pro Ala Asp Ala Gly Thr Tyr Tyr Cys Val
                 85                  90                  95

Lys Phe Arg Lys Gly Ser Pro Asp Asp Val Glu Phe Lys Ser Gly Ala
            100                 105                 110

Gly Thr Glu Leu Ser Val Arg Ala
            115                 120
```

<210> SEQ ID NO 8
<211> LENGTH: 119

```
<212> TYPE: PRT
<213> ORGANISM: mouse

<400> SEQUENCE: 8

Ala Thr Gly Lys Glu Leu Lys Val Thr Gln Pro Glu Lys Ser Val Ser
1               5                   10                  15

Val Ala Ala Gly Asp Ser Thr Val Leu Asn Cys Thr Leu Thr Ser Leu
            20                  25                  30

Leu Pro Val Gly Pro Ile Arg Trp Tyr Arg Gly Val Gly Pro Ser Arg
        35                  40                  45

Leu Leu Ile Tyr Ser Phe Ala Gly Glu Tyr Val Pro Arg Ile Arg Asn
    50                  55                  60

Val Ser Asp Thr Thr Lys Arg Asn Asn Met Asp Phe Ser Ile Arg Ile
65                  70                  75                  80

Ser Asn Val Thr Pro Ala Asp Ala Gly Ile Tyr Tyr Cys Val Lys Phe
                85                  90                  95

Gln Lys Gly Ser Ser Glu Pro Asp Thr Glu Ile Gln Ser Gly Gly Gly
            100                 105                 110

Thr Glu Val Tyr Val Leu Ala
        115

<210> SEQ ID NO 9
<211> LENGTH: 119
<212> TYPE: PRT
<213> ORGANISM: mouse

<400> SEQUENCE: 9

Ala Thr Gly Lys Glu Leu Lys Val Thr Gln Pro Glu Lys Ser Val Ser
1               5                   10                  15

Val Ala Ala Gly Asp Ser Thr Val Leu Asn Cys Thr Leu Thr Ser Leu
            20                  25                  30

Leu Pro Val Gly Pro Ile Arg Trp Tyr Arg Gly Val Gly Pro Ser Arg
        35                  40                  45

Leu Leu Ile Tyr Ser Phe Ala Gly Glu Tyr Val Pro Arg Ile Arg Asn
    50                  55                  60

Val Ser Asp Thr Thr Lys Arg Asn Asn Met Asp Phe Ser Ile Arg Ile
65                  70                  75                  80

Ser Asn Val Thr Pro Ala Asp Ala Gly Ile Tyr Tyr Cys Val Lys Phe
                85                  90                  95

Gln Lys Gly Ser Ser Glu Pro Asp Thr Glu Ile Gln Ser Gly Gly Gly
            100                 105                 110

Thr Glu Val Tyr Val Leu Ala
        115

<210> SEQ ID NO 10
<211> LENGTH: 117
<212> TYPE: PRT
<213> ORGANISM: mouse

<400> SEQUENCE: 10

Ala Thr Arg Thr Glu Val Lys Val Ile Gln Pro Glu Lys Ser Val Ser
1               5                   10                  15

Val Ala Ala Gly Asp Ser Thr Val Leu Asn Cys Thr Leu Thr Ser Leu
            20                  25                  30

Leu Pro Val Gly Pro Ile Arg Trp Tyr Arg Gly Val Gly Gln Ser Arg
        35                  40                  45

Gln Leu Ile Tyr Ser Phe Thr Thr Glu His Phe Pro Arg Val Thr Asn
```

Val Ser Asp Ala Thr Lys Arg Ser Asn Leu Asp Phe Ser Ile Arg Ile
65                  70                  75                  80

Ser Asn Val Thr Pro Glu Asp Ala Gly Thr Tyr Tyr Cys Val Lys Phe
                85                  90                  95

Gln Arg Gly Ser Pro Asp Thr Glu Ile Gln Ser Gly Gly Gly Thr Glu
            100                 105                 110

Val Tyr Val Leu Ala
        115

<210> SEQ ID NO 11
<211> LENGTH: 119
<212> TYPE: PRT
<213> ORGANISM: mouse

<400> SEQUENCE: 11

Ala Thr Gly Thr Glu Val Lys Val Thr Gln Pro Glu Lys Ser Val Ser
1               5                   10                  15

Val Ala Ala Gly Asp Ser Thr Ile Leu Asn Cys Thr Val Thr Ser Leu
            20                  25                  30

Leu Pro Val Gly Pro Ile Arg Trp Tyr Arg Gly Val Gly Gln Ser Arg
        35                  40                  45

Leu Leu Ile Tyr Ser Phe Thr Gly Glu His Phe Pro Arg Val Arg Asn
    50                  55                  60

Val Ser Asp Thr Thr Lys Arg Asn Asn Met Asp Phe Ser Ile Arg Ile
65                  70                  75                  80

Ser Asn Val Thr Pro Glu Asp Ala Gly Thr Tyr Tyr Cys Val Lys Phe
                85                  90                  95

Gln Arg Gly Ser Glu Pro Asp Thr Glu Ile Gln Ser Gly Gly Gly
            100                 105                 110

Thr Glu Val Tyr Val Leu Ala
        115

<210> SEQ ID NO 12
<211> LENGTH: 119
<212> TYPE: PRT
<213> ORGANISM: mouse

<400> SEQUENCE: 12

Val Thr Gly Lys Glu Leu Lys Val Thr Gln Pro Glu Lys Ser Val Ser
1               5                   10                  15

Val Ala Ala Gly Asp Ser Thr Val Leu Asn Cys Thr Leu Thr Ser Leu
            20                  25                  30

Leu Pro Val Gly Pro Ile Lys Trp Tyr Arg Gly Val Gly Gln Ser Arg
        35                  40                  45

Leu Leu Ile Tyr Ser Phe Thr Gly Glu His Phe Pro Arg Val Thr Asn
    50                  55                  60

Val Ser Asp Ala Thr Lys Arg Asn Asn Met Asp Phe Ser Ile Arg Ile
65                  70                  75                  80

Ser Asn Val Thr Pro Glu Asp Ala Gly Thr Tyr Tyr Cys Val Lys Phe
                85                  90                  95

Gln Lys Gly Pro Ser Glu Pro Asp Thr Glu Ile Gln Ser Gly Gly Gly
            100                 105                 110

Thr Glu Val Tyr Val Leu Ala
        115

```
<210> SEQ ID NO 13
<211> LENGTH: 368
<212> TYPE: PRT
<213> ORGANISM: human

<400> SEQUENCE: 13

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Pro Pro Cys Pro Ser Cys Pro Ala Pro Glu Phe Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser Gln Glu Asp Pro
            180                 185                 190

Glu Val Gln Phe Asn Trp Tyr Val Asp Gly Val Glu Val His Asn Ala
        195                 200                 205

Lys Thr Lys Pro Arg Glu Glu Gln Phe Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Gly Leu Pro Ser Ser Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Gln Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Arg Leu Thr Val Asp Lys Ser
                325                 330                 335

Arg Trp Gln Glu Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```